US010048224B2

(12) United States Patent
Goodwill et al.

(10) Patent No.: US 10,048,224 B2
(45) Date of Patent: Aug. 14, 2018

(54) TECHNIQUES FOR MAGNETIC PARTICLE IMAGING

(71) Applicant: The Regents of the University of California, Oakland, CA (US)

(72) Inventors: Patrick W. Goodwill, San Francisco, CA (US); Steven M. Conolly, Palo Alto, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 694 days.

(21) Appl. No.: 14/328,560

(22) Filed: Jul. 10, 2014

(65) Prior Publication Data
US 2015/0008910 A1    Jan. 8, 2015

Related U.S. Application Data

(62) Division of application No. 12/737,214, filed as application No. PCT/US2009/003764 on Jun. 23, 2009, now Pat. No. 8,847,592.
(Continued)

(51) Int. Cl.
G01N 27/72    (2006.01)
A61B 5/05    (2006.01)
(Continued)

(52) U.S. Cl.
CPC ............... *G01N 27/72* (2013.01); *A61B 5/05* (2013.01); *A61B 5/0515* (2013.01); *G01R 33/00* (2013.01);
(Continued)

(58) Field of Classification Search
CPC ........ G01N 27/72; A61B 5/05; A61B 5/0515; G01R 33/00; G01R 33/0213; G01R 33/10; G01R 33/1269; G01R 33/1276
See application file for complete search history.

(56) References Cited

U.S. PATENT DOCUMENTS 4,538,130 A    8/1985    Gluckstern et al.
4,545,384 A    10/1985    Kawachi
(Continued)

FOREIGN PATENT DOCUMENTS

WO    2004091395    10/2004
WO    2008099331    10/2004
(Continued)

OTHER PUBLICATIONS

Goodwill, Narrowband and x-Space Magnetic Particle Imaging, dissertation, 2010.*
(Continued)

*Primary Examiner* — Daniel Miller
(74) *Attorney, Agent, or Firm* — Venable LLP; Henry J. Daley; Laura G. Remus

(57) ABSTRACT

A magnetic particle imaging apparatus includes magnets [106,107] that produce a gradient magnetic field having a field free region (FFR), excitation field electromagnets [102, 114] that produce a radiofrequency magnetic field within the field free region, high-Q receiving coils [112] that detect a response of magnetic particles in the field free region to the excitation field. Field translation electromagnets create a homogeneous magnetic field displacing the field-free region through the field of view (FOV) allowing the imaging region to be scaled to optimize scan time, scanning power, amplifier heating, SAR, dB/dt, and/or slew rate. Efficient multi-resolution scanning techniques are also provided. Inter-modulated low and radio-frequency excitation signals are processed to produce an image of a distribution of the magnetic nanoparticles within the imaging region. A single composite image is computed using deconvolution of multiple signals at different harmonics.

23 Claims, 18 Drawing Sheets

Related U.S. Application Data

(60) Provisional application No. 61/074,931, filed on Jun. 23, 2008.

(51) Int. Cl.
  *G01R 33/02* (2006.01)
  *G01R 33/10* (2006.01)
  *G01R 33/12* (2006.01)
  *G01R 33/00* (2006.01)
  *A61B 5/00* (2006.01)

(52) U.S. Cl.
  CPC ......... *G01R 33/0213* (2013.01); *G01R 33/10* (2013.01); *G01R 33/1269* (2013.01); *G01R 33/1276* (2013.01); *A61B 5/7257* (2013.01)

(56) References Cited

U.S. PATENT DOCUMENTS

| | | |
|---|---|---|
| 5,004,983 A | 4/1991 | Proksa et al. |
| 5,510,711 A | 4/1996 | Molyneaux et al. |
| 2003/0085703 A1 | 5/2003 | Gleich |
| 2005/0073309 A1 | 4/2005 | Williams et al. |
| 2006/0211938 A1 | 9/2006 | Gleich et al. |
| 2006/0248944 A1 | 11/2006 | Gleich |
| 2007/0258908 A1 | 11/2007 | Lanza et al. |
| 2008/0218162 A1 | 9/2008 | Ruhrig |
| 2008/0309330 A1 | 12/2008 | Ohyu et al. |
| 2009/0115415 A1 | 5/2009 | Weaver et al. |
| 2010/0033171 A1 | 2/2010 | Gleich et al. |
| 2010/0052668 A1 | 3/2010 | Gleich et al. |

FOREIGN PATENT DOCUMENTS

| | | |
|---|---|---|
| WO | 2010008478 | 1/2010 |
| WO | 2011010243 | 1/2011 |

OTHER PUBLICATIONS

Knopp et al., Trajectory analysis for magnetic particle imaging, Dec. 2008, p. 386.*
Kovacs, Scanning strategies for imaging arrays, Proc.SPIE Int.Soc. Opt.Eng.7020:5,2008.*
Gleich et al, Tomographic imaging using the nonlinear response of magnetic particles, Nature, 435(7046):1214-7, Jun. 2005.*
Goodwill and Conolly "Multidimensional x-space Magnetic particle imaging," Ieee Transactions on Medical Imaging, 30(9): (2011) 1581-1590 ISSN 1558-254X.

* cited by examiner

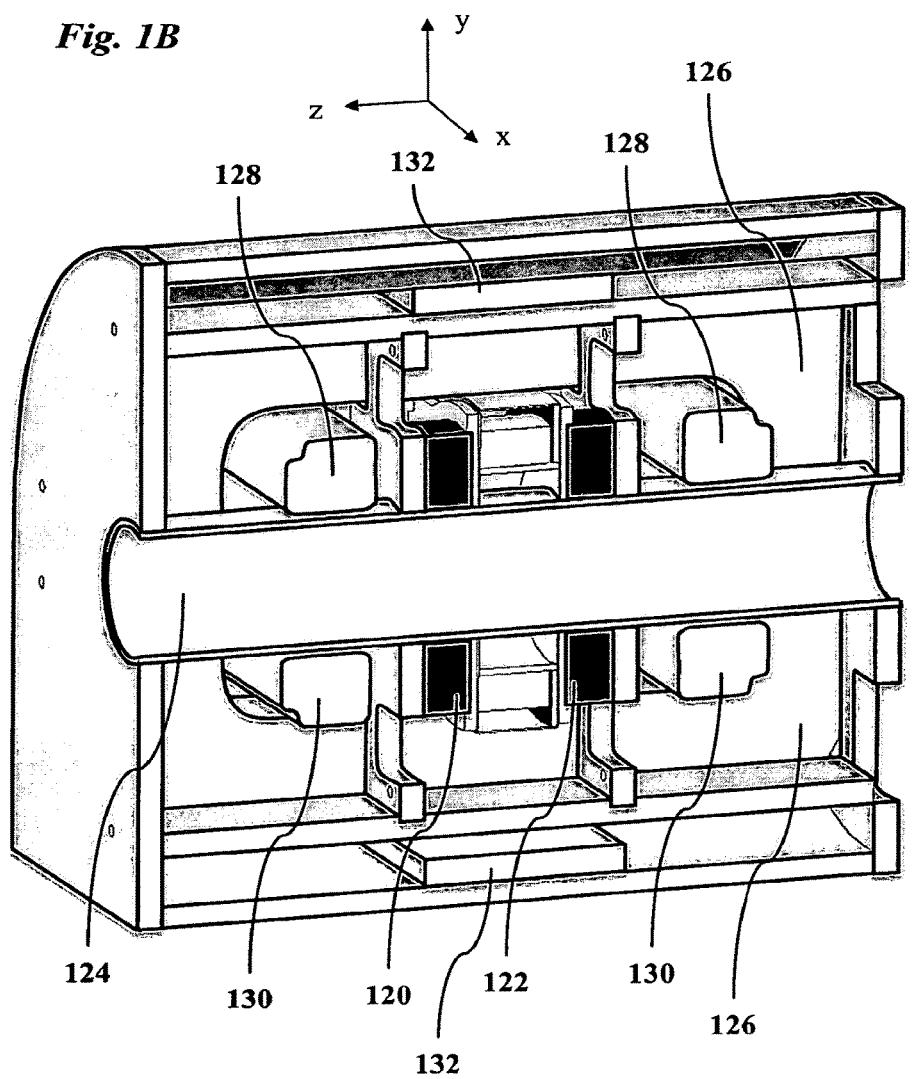

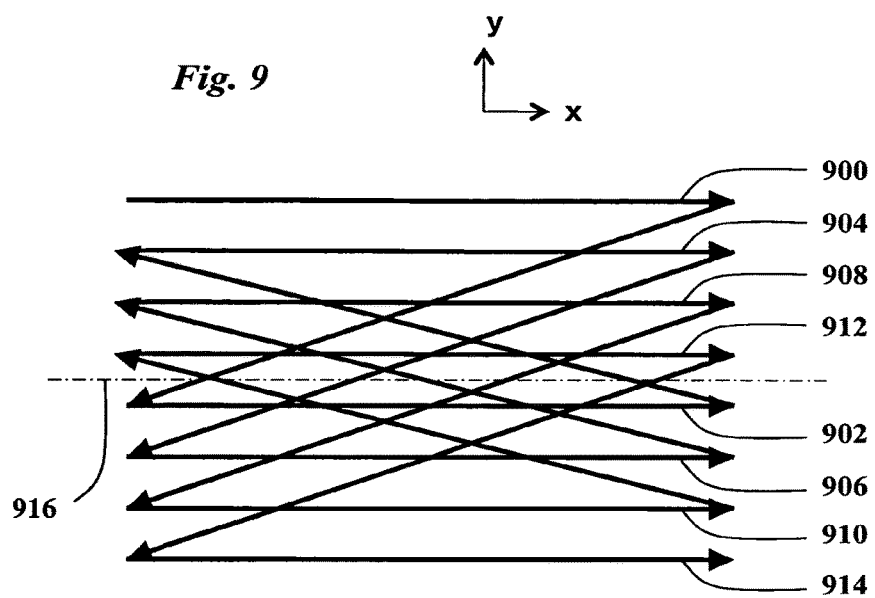
*Fig. 9*
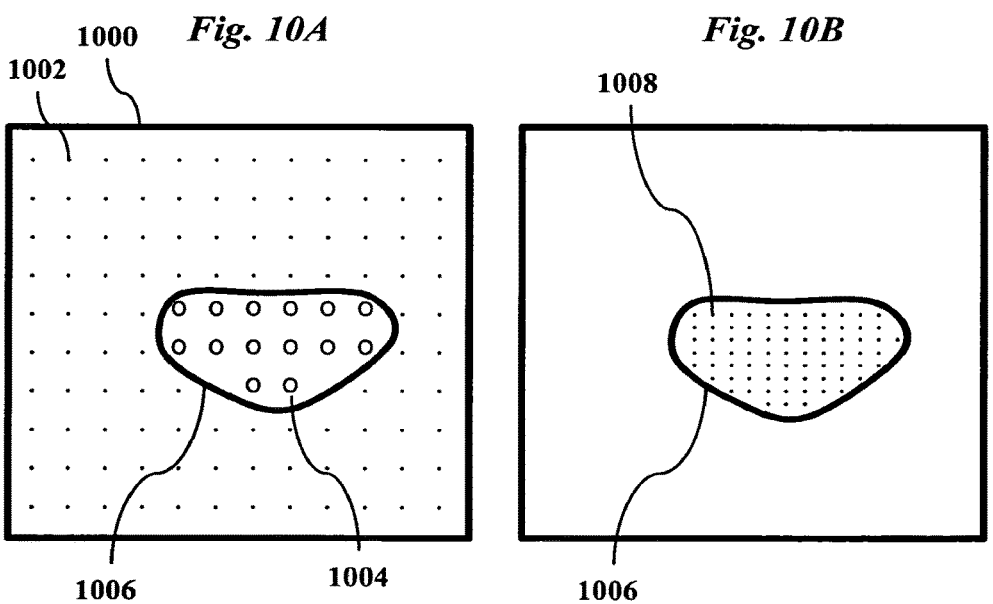
*Fig. 10A*   *Fig. 10B*

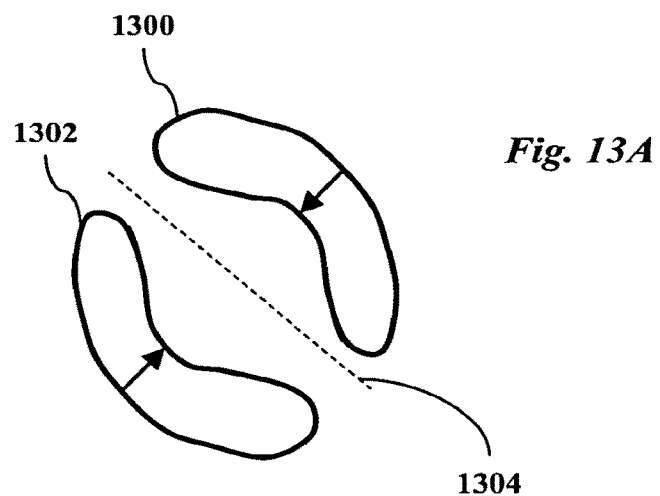
*Fig. 13A*
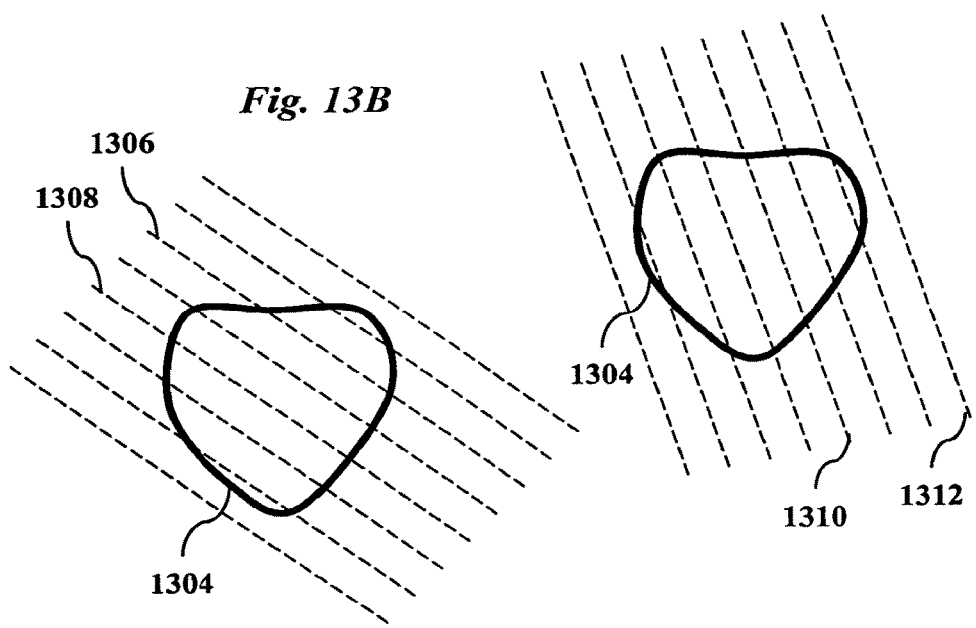
*Fig. 13C*
*Fig. 13B*

TECHNIQUES FOR MAGNETIC PARTICLE IMAGING

CROSS-REFERENCE TO RELATED APPLICATIONS

This patent application is a divisional of U.S. patent application Ser. No. 12/737,214, filed Dec. 16, 2010, which is a national stage application of PCT Application No. PCT/US2009/003764, filed Jun. 23, 2009, which claims priority to U.S. Provisional Patent Application No. 61/074,931, filed Jun. 23, 2008, the disclosures of each of which are hereby incorporated by reference in their entirety.

FIELD OF THE INVENTION

The present invention relates generally to methods and devices for volume imaging. More specifically, it relates to improved techniques for magnetic particle imaging.

BACKGROUND OF THE INVENTION

Magnetic particle imaging (MPI) is a young and developing volumetric imaging technique first proposed in 2005 that directly detects the magnetization from magnetic particles without depth limitations. MPI has important applications to medical imaging, e.g., heart and blood vessel imaging, cell tracking, and cancer detection. The basic principle of MPI involves exciting magnetic particles in a selected region (e.g., magnetic particle contrast agents injected into the blood stream or labeled into or on cells) and detecting their non-linear response. An inhomogeneous magnetic field having a field-free region and a strong field outside this region selects the particles that will be detected. Such a field may be established, for example, using two permanent magnets with opposing magnetic field orientations. Magnetic particles located outside the field-free region become magnetically saturated by the strong field. Non-saturated magnetic particles located inside the field-free region are excited by generating an oscillating magnetic field superimposed on the inhomogeneous field.

The oscillating field may be generated, for example, using solenoids. The excited particles are detected by measuring their non-linear response to the oscillating field. Because tissue has a negligible nonlinear response, detecting the nonlinear harmonics from the magnetic particles provides a high contrast signal. The magnetic particles are normally composed of a non-linear ferromagnetic material, e.g., ferumoxide or super-paramagnetic iron oxide (SPIO). Volumetric imaging is performed by changing the relative position of the field-free region with respect to the distribution of the magnetic particles (e.g., by altering the inhomogeneous field to displace the field-free region and/or moving the object being imaged).

In MPI techniques proposed by Gleich and Weizenecker (US 2003/0085703, WO 2004/091395, WO 2008/099331), the magnetic field used to excite the magnetic particles oscillates at a frequency $f_0$ in the radiofrequency range, and signals at a series of harmonics at $2f_0$, $3f_0$, $4f_0$, ..., $20f_0$, are measured using a receiver coil. Because these harmonics span a large bandwidth, detecting them poses challenges for the receiver design. For example, with $f_0$=25.5 kHz, the harmonics span a large 500 kHz bandwidth. Gleich et al. use an un-tuned receiver coil, which can not be optimally matched to the preamplifier, to detect the signals over this large bandwidth.

Gleich and Weizenecker teach a technique for creating an image from a set of N harmonics of the fundamental excitation frequency. However, there are several challenges with their technique. First, their method casts the image data over a very broad frequency range, precluding narrow-band detection and associated benefits. Also, their image reconstructed from the N harmonic images is not optimal. Moreover, conventional deconvolution algorithms can lead to pernicious noise amplification when applied outside of their original context of a single image blurred by a single point spread function. Thus, it would be an advance in the state of the art to provide a method for combining N images from separate harmonics to create a single high resolution image with minimal noise amplification.

In the method of Gleich and Weizenecker, each high resolution pixel is sampled, requiring $M_x*M_y*M_z$ samples, where $M_x$ is the number of voxels in x direction, $M_y$ is the number of voxels in the y direction, and $M_z$ is the number of voxels in the z direction. However, the magnetic particle contrast agent is likely to be substantially sparse, meaning many of these voxels are substantially void of contrast and, hence, signal. Consequently, the sampling method is inefficient and slow. It would thus be an advance in the state of the art to provide more efficient methods for MPI imaging.

SUMMARY OF THE INVENTION

In one aspect, a magnetic particle imaging apparatus includes permanent magnets that produce a gradient magnetic field having a field free region (FFR), excitation field electromagnets and associated excitation circuitry that produce a radiofrequency magnetic field within the field free region, receiving coils and associated receiving circuitry that detect a response of magnetic particles in the field free region to the excitation field, and signal processing circuitry that convert the detected response to a digital representation of a distribution of the magnetic particles.

In some embodiments, the permanent magnets are coaxially arranged ring magnets producing a gradient field at least two times larger in magnitude in an axial direction than in a transverse direction. The gradient field in the transverse direction is approximately linear near the field-free region. In some embodiments, the field free region is localized at a point. In other embodiments, the permanent magnets produce a gradient magnetic field having a field free region that is extended linearly. In other embodiments, the permanent magnets include a ring magnet array.

Preferred embodiments include field translation electromagnets that create a homogeneous magnetic field displacing the field-free region through the field of view (FOV). The field translation electromagnets may include one, two, or three sets of electromagnets oriented in three corresponding mutually orthogonal directions. In other embodiments, the field-free region is translated by physical movement of the object relative to the permanent magnets, or a combination of physical movement and electromagnets.

In some embodiments implementing intermodulation MPI, the excitation field electromagnets comprise low-frequency excitation electromagnets driven by a low-frequency excitation signal and radio-frequency excitation electromagnets driven by a radio-frequency excitation signal. The excitation field electromagnets may include multiple pairs of electromagnets, wherein the multiple pairs are oriented in mutually orthogonal directions. Preferably, the excitation circuitry includes a filter that suppresses harmonics of the fundamental radio frequency excitation signal. The excitation circuitry preferably also includes feedback circuitry that prevents phase and magnitude drift in excitation field strength.

The receiving coils are preferably high-Q coils (i.e., Q>10), each tuned to one or two harmonics of a radio frequency excitation signal. The receiving circuitry includes amplifiers preferably matched to the receiving coils. The receiving circuitry also includes multiple filters that attenuate a fundamental of a radio frequency excitation signal.

In some embodiments implementing intermodulation MPI, the signal processing circuitry includes a frequency down-converter circuit block that separately down-converts multiple intermodulation signals present in the detected response.

In another aspect, a method of magnetic particle imaging is provided. The method includes placing magnetic particles into an imaging region, generating within the imaging region an inhomogeneous magnetic field having a spatial gradient and having a field-free region within the imaging region, generating within the imaging region a scanning magnetic field that causes the field-free region to follow a trajectory within the imaging region, generating within the imaging region a first excitation magnetic field having an oscillation frequency $f_0$, generating within the imaging region a second excitation magnetic field having an oscillation frequency $f_1 < f_0$, detecting each of a plurality of N intermodulation signals, and processing the detected intermodulation signals to produce an image of a distribution of the magnetic nanoparticles within the imaging region. The intermodulation signals include signals at frequencies $m*f_0 + n*f_1$ for integers m and n where $m \geq 1$. Preferably, $1 < N < 40$. The intermodulation signals are produced by nonlinear mixing of the first oscillating magnetic field and the second oscillating magnetic field within magnetic particles distributed within the imaging region. The first excitation magnetic field and the second excitation magnetic field are preferably operated concurrently. Preferably, the detecting uses a high-Q receiver coil and preamplifier tuned to receive intermodulation signals within a bandwidth $(2N+1)*f_1$ containing a frequency $m*f_0$.

The second excitation magnetic field may have a sinusoidal waveform or a non-sinusoidal waveform. In addition, the waveform shape of the second excitation magnetic field may be dynamically changed during the imaging.

In some embodiments, a single composite image is produced from the detected intermodulation signals by computing a frequency-domain representation of the detected intermodulation signals, deconvolving the frequency-domain representation to produce a single composite frequency-domain image from said frequency-domain representation of the detected intermodulation signals, thresholding poorly conditioned frequency domain points, and converting the composite frequency-domain image to a spatial-domain image.

In another aspect, a method of magnetic particle imaging is provided that includes placing magnetic particles into an imaging region, generating within the imaging region an inhomogeneous magnetic field having a spatial gradient and having a field-free region within the imaging region, generating within the imaging region a scanning magnetic field that displaces the position of the field-free region, generating an excitation magnetic field that excites the magnetic particles positioned at the field-free region, detecting signals produced by the magnetic particles distributed within the imaging region, and producing from the detected signals an image of the distribution of the magnetic particles within the imaging region. The scanning magnetic field causes the position of the field-free region to follow a predetermined trajectory that optimizes one or more properties such as scan time, scanning power, amplifier heating, SAR, dB/dt, and/or slew rate. The signals detected at a given time are produced by magnetic particles located at positions coincident with a position of the field-free region at the given time. The magnetic particles saturate their domains in a magnetic field and may be super-paramagnetic iron oxide nanoparticles. The magnetic particles may be placed in the imaging region by placing in the imaging region an object that contains a distribution of the magnetic particles. For example, the magnetic particles could be distributed within the object through injection, attached or embedded or released from a device such as a canula or catheter, attached to or inside cells and injected, or functionalized with ligands and injected. The excitation magnetic field may have a low-frequency component and a radio-frequency component.

In some embodiments, the predetermined trajectory may include a sequence of scan lines, such that an average displacement between pairs of sequential scan lines is approximately constant. For example, the predetermined trajectory may alternate between scan lines positioned on opposite sides of a central position of the field-free region. The trajectory may also include a set of parallel scan lines such that the trajectory moves in the same direction for all the parallel scan lines. Alternatively, the trajectory may have a spiral pattern such that slew rate and scan time are optimized, or it may have a serpentine pattern. In some embodiments, the scanning magnetic field causes the position of the field-free region to move along a first axis at a first average rate and to move along a second axis at a second average rate, such that the first axis is perpendicular to the second axis, and a ratio of the first average rate to the second average is between 32 and 1024.

In another aspect, a method of magnetic particle imaging is provided that includes placing magnetic particles into an imaging region, generating within an imaging region an inhomogeneous magnetic field having a spatial gradient and having a field-free region within the imaging region, generating within the imaging region a scanning magnetic field that causes the field-free region to change position within the imaging region following a predetermined trajectory, generating an excitation magnetic field that excites the magnetic particles positioned at the field-free region, detecting signals produced by the magnetic particles distributed within the imaging region, where the signals detected at a given time are produced by magnetic particles located at positions coincident with a position of the field-free region at the given time, and where the detected signals comprise multiple images, and producing a single composite image from the multiple images by computing a frequency-domain representation of the multiple images, deconvolving the frequency-domain representation to produce a single composite frequency-domain image from said frequency-domain representation of the multiple images, and converting the composite frequency-domain image to a spatial-domain image. The method may also include reducing the magnitudes of signals at points in the frequency domain representation of the composite image where points of a point spread function in the frequency-domain have magnitudes below a predetermined threshold. Preferably, converting the composite frequency-domain image to a spatial-domain image is performed using a multidimensional fast Fourier transform. In some embodiments, the excitation magnetic field includes a low-frequency component and a radio-frequency component, and the multiple images include images corresponding to different intermodulation signal products. In some embodiments, before converting to the frequency domain, the harmonic images are stretched with a rubber sheeting algorithm in order to reduce distortion effects of a magnetic field in the apparatus that is not perfectly linear. Preferably, the stretching results in an undistorted image.

In another aspect, a method of magnetic particle imaging is provided that includes placing into an imaging region an object containing a distribution of magnetic particles, generating within the imaging region an inhomogeneous magnetic field having a spatial gradient and having a field-free region within the imaging region, generating within the imaging region a scanning magnetic field that causes the field-free region to follow a trajectory within the imaging region, generating within the imaging region an excitation magnetic field that excites the magnetic particles, detecting signals from the magnetic nanoparticles distributed within the imaging region, producing from the detected signals a first image of the distribution of the magnetic particles within the imaging region, and producing from the detected signals a second image of the distribution of the magnetic particles by performing a fine-grained sampling of the detected signals only for voxels in the first image whose intensities exceeds a predetermined threshold.

In some embodiments, a second trajectory is computed from the first image of the distribution of the magnetic particles, and the scanning magnetic field is modified to cause the field-free region to follow the second trajectory within the imaging region. Preferably, the method is efficiently performed so that the first image and second image are produced in real time. In some embodiments, the scanner follows a first low resolution trajectory. If magnetic particles are found at a specific point in the low resolution trajectory, the scanner immediately scans a second trajectory in a neighborhood of that point with higher spatial resolution. The scanner then moves to the next point in the first trajectory.

BRIEF DESCRIPTION OF THE DRAWINGS

FIG. 1B is a perspective cut-away view of a magnetic subsystem of a device according to an embodiment of the invention.

FIG. 9 illustrates an example of a power-efficient scanning trajectory according to one embodiment of the invention.

FIGS. 10A and 10B illustrate a technique of adaptive multi-resolution scanning according to an embodiment of the invention.

FIG. 13A is a cross-sectional illustration of a pair of specially designed magnets that produce a strong field gradient and a field-free line, according to an embodiment of the invention.

FIGS. 13B and 13C illustrate an MPI computed tomography imaging technique using a field-free line to acquire projection image slices at different angles.

DETAILED DESCRIPTION

Figure 1A:
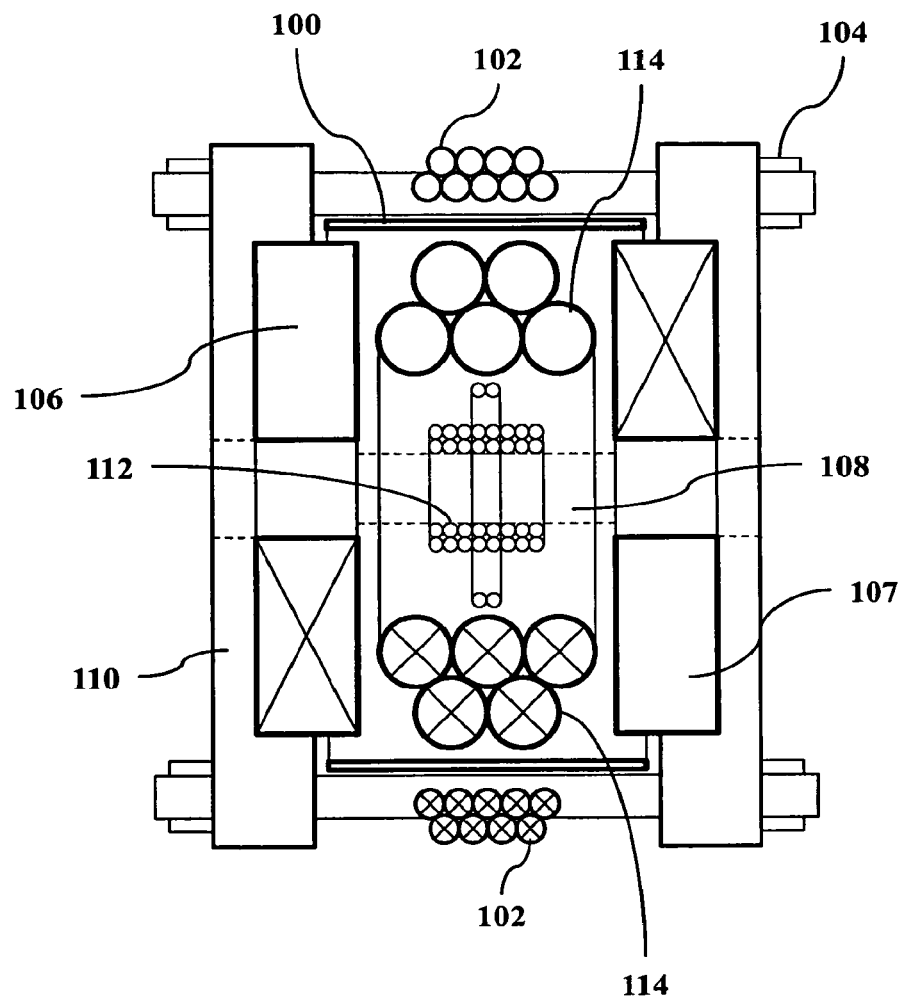
FIG. 1A is a cross-sectional view of an MPI apparatus according to an embodiment of the invention.

An MPI apparatus according to an embodiment of the invention is shown in FIG. 1A. NdFeB ring magnets 106, 107 create a static inhomogeneous magnetic gradient field having a field-free region located near the center of imaging bore 108. Ring magnets 106, 107 have a mean diameter of 7.62 cm and a center-to-center separation of 6.85 cm. The magnetic field is approximately linear axially down the bore, with a gradient of $dB/dz=4.5$ T/m. Coronal gradients are $dB/dx=dB/dy=2.6$ T/m. Water-cooled excitation solenoid 114 generates a dynamic magnetic field that is superimposed on the static field and can excite magnetic particles in the imaging bore 108. In addition, intermodulation solenoid 102 generates a dynamic magnetic field that is also superimposed on the static field. Magnetic shield 100 passively isolates the AC excitation solenoids 102 and 114 from interaction with other components to reduce unwanted heating and signal interference. Signals from magnetic particles located in the imaging bore 108 are received by concentric gradiometer receive coil 112. The mechanical frame for the apparatus includes G10 plate 110 for mounting ring magnets 106, 107 and aluminum bolt 104.

FIG. 1B is a perspective cut-away view of a device according to an embodiment of the invention. The device contains NdFeB permanent magnets 120, 122 that produce an inhomogeneous field with a field-free point in the center of the bore 124, water cooled electromagnet coils (not shown) positioned inside bore 124 to generate a radio-frequency excitation magnetic field along the longitudinal z-axis and water cooled electromagnet coils 128, 130, 132 to generate low-frequency excitation magnetic fields along the x-axis, y-axis, and z-axis, respectively. The x, y, and z axis electromagnets also generate a scanning magnetic field to move the field-free-point.

The permanent magnets produce a z-gradient of 8 T/m and x-y-gradient of 4 T/m. In one implementation, the inner diameter is 3 inches and the outer diameter is 12 inches, and the interior is potted with epoxy to eliminate vibration. The RF excitation coils (not shown) positioned inside bore 124 are driven by a 750 Watt continuous power amplifier. The LF coils are driven by a 800 Amp peak-to-peak amplifier.

Circuitry

Figure 4A:
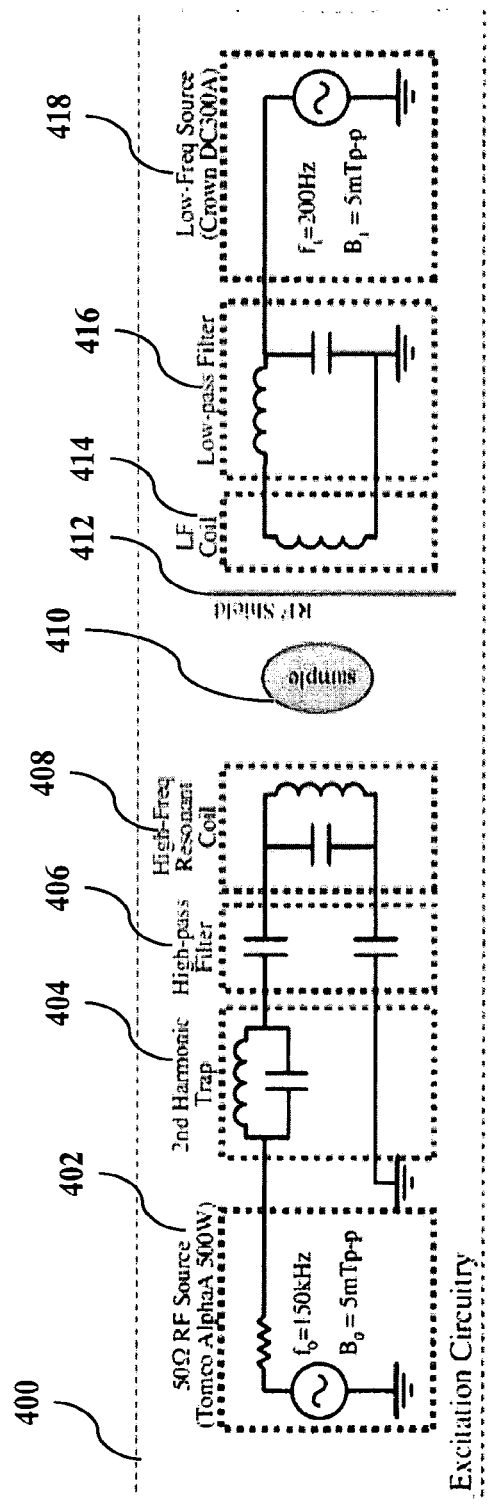
FIGS. 4A and 4B are schematic diagrams of the transmit and receive chains, respectively, according to an embodiment of the invention.
Figure 4B:
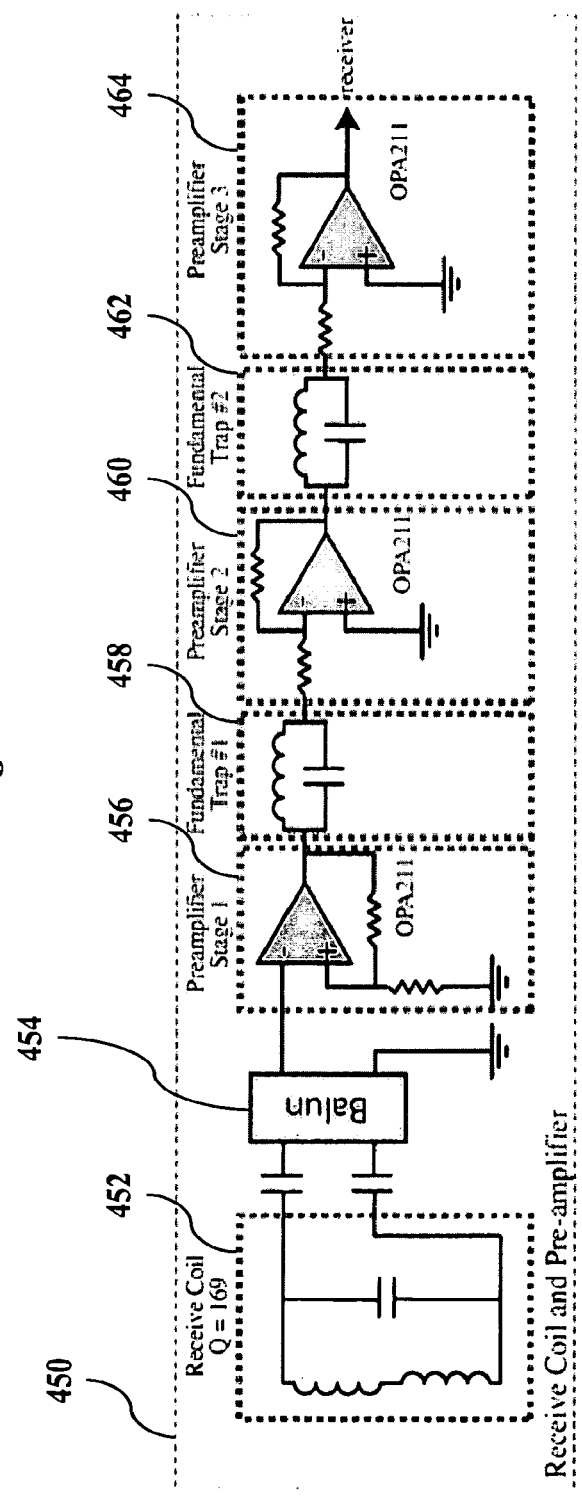

FIGS. 4A and 4B are schematic diagrams of the transmit and receive chains, respectively. The excitation circuitry 400 shown in FIG. 4A includes an RF power amplifier 402, second harmonic trap 404, high-pass filter 406, and high-frequency resonant coil 408. The excitation circuitry 100 also includes an LF power amplifier 418, low-pass filter 416, and LF coil 414 isolated from the sample 410 and RF chain by RF shield 412. The RF and LF signals are generated by these chains to excite magnetic particles in sample 410. The signal generators are phase locked to a coherent detector. The RF amplifier 402 drives the matched, water-cooled resonant transmit coil 408 to generate a sinusoidal magnetic field at $f_0$=150 kHz with peak-to-peak amplitude of 6 mT. The intermodulation coil 414, driven by audio amplifier 418, generates a sinusoidal magnetic field at $f_0$=200 Hz with peak-to-peak amplitude of 5.9 mT.

The receive circuitry 450 shown in FIG. 4B includes a receive coil 452, balun 454, first preamplifier stage 456, first fundamental trap 458, second preamplifier stage 460, second fundamental trap 462, and preamplifier stage 464.

Figure 3A:
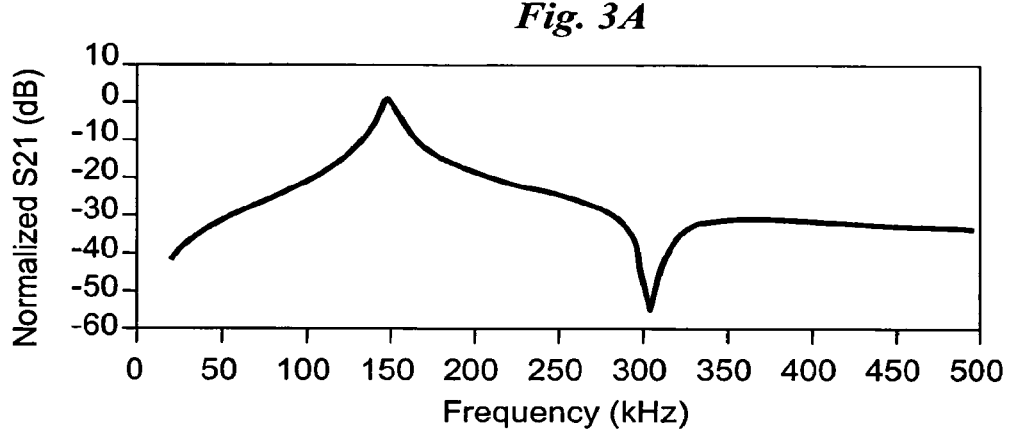
FIGS. 3A and 3B are graphs of the transfer functions for transmit and receive chains of an apparatus according to an embodiment of the invention.
Figure 3B:
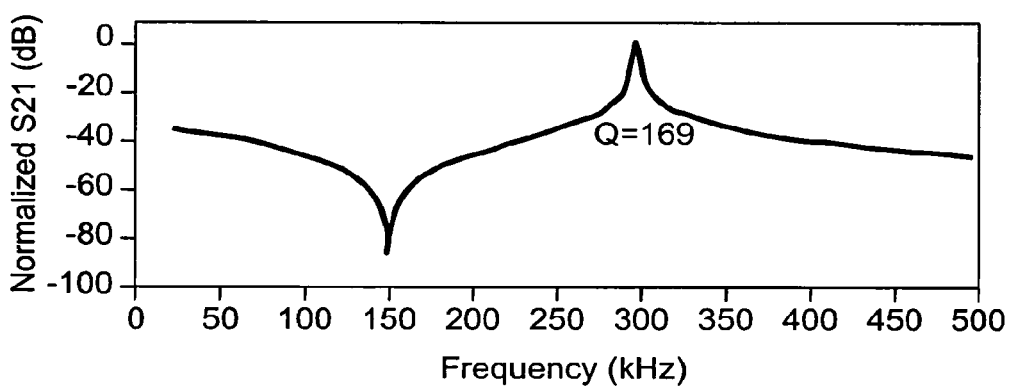

Interfacing electronics are designed to prevent intermodulation in the RF and LF amplifier output stages (FIG. 4A) and in the preamplifier (FIG. 4B) through the use of high-pass, low-pass, and notch filters. The RF transmit chain 400 has a resonant transmit coil 408 at 150 kHz and a second harmonic trap 404 at 300 kHz. The receive chain 450 has a fundamental harmonic trap 458 at 150 kHz and high-Q receive coil 452 at 300 kHz. The transfer functions for the transmit and receive chains are shown, respectively, in FIGS. 3A and 3B which show a minimum of 80 dBV of isolation between transmit and receive frequencies. Each isolation stage, including RF shield, provides approximately 30 dB of isolation. All inductors are high-Q RF toroids or are air core. High power capacitors are used in the transmit chain and high-Q capacitors in the receive chain.

Figure 4C:
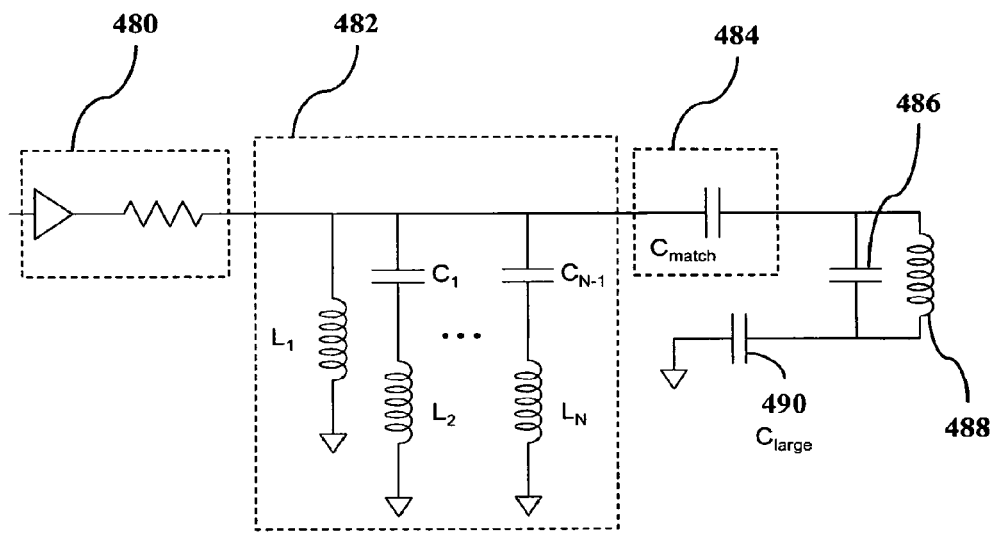
FIG. 4C is a schematic diagram of the transmit chain according to an embodiment of the invention.

FIG. 4C is a schematic diagram of the transmit chain according to another embodiment of the invention. The RF transmit chain includes RF amplifier 480, $2f_0$ filter 482, matching capacitor 484, high-power capacitor 486, RF coil 488, and large capacitor 490. The filter 482 reduces the effect of harmonics in the output spectrum of the RF amplifier. The filter circuit elements inductors $L_1$, $L_2$, and capacitor $C_1$ resonate so that the fundamental frequency $f_0$ passes through the filter. Inductor $L_2$ and capacitor $C_1$ are tuned so that there is a shunt to ground at $2f_0$. Additional shunts at $3f_0$, $4f_0$, and higher can be added as well, up to shunt at $N f_0$ provided by and capacitor $C_N$.

The battery-powered preamplifier uses low-noise op-amps in stages 456, 460, 464 matched to a high-Q coil 452 of $Z_{coil}$=2 kΩ at resonance. The preamplifier is noise matched to the receive coil using a 4:1 balanced-to-unbalanced impedance transformer (balun) 454.

Some embodiments may include feedback circuitry to prevent phase and magnitude drift in the RF transmit power and excitation field strength caused by loading of the transmit coil and heating. The feedback can be implemented in various ways such as cartesian feedback or current feedback. The current or field can be measured in various ways such as using a pickup coil (preferably untuned so that loading is not an issue) or a current sensor or a shunt resistor. The objective of the feedback is to regulate the field that the sample experiences, and is effectively defining the current through the transmit coil. Also, because the RF signal is in the kHz to low MHz range, simple feedback may also be practical.

In some embodiments, feedback damping is used to widen the bandwidth of the receive coils. Feedback damping is performed by feeding back the received signal out of phase to the receive coil. This can be seen in FIG. 4D.

In some embodiments, a rotating (quadrature) excitation field is used to increase the detectable signal.

Signal Harmonics and Sideband Tones

Figure 2A:
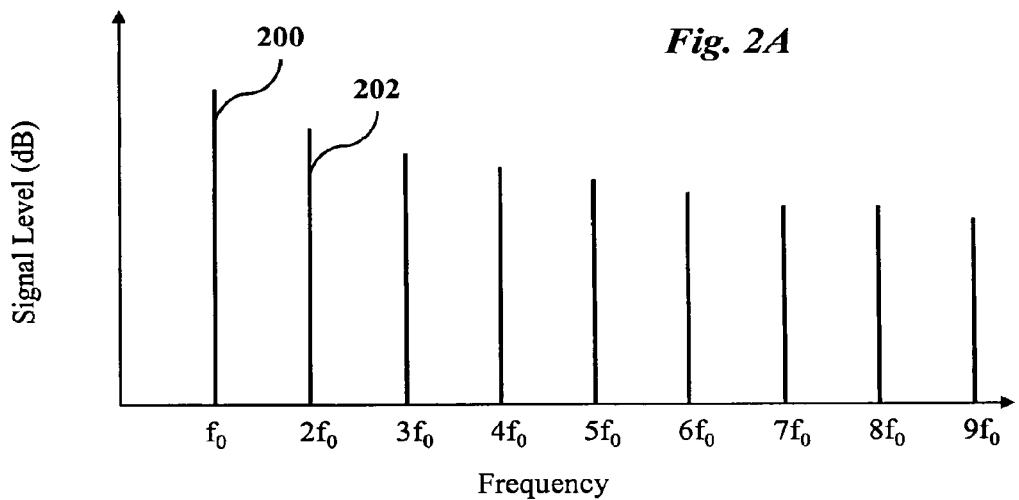
FIG. 2A is a graph of received signal level versus frequency for a conventional MPI technique showing multiple received harmonics.

FIG. 2A is a graph of received signal level versus frequency for a conventional MPI technique showing multiple received harmonics such as second harmonic ($2f_0$) 202. The graph shows a simulated signal received by an untuned pickup coil. The fundamental ($f_0$) 200 is typically not used because it is contaminated by direct feed through from the excitation field.

Figure 2B:
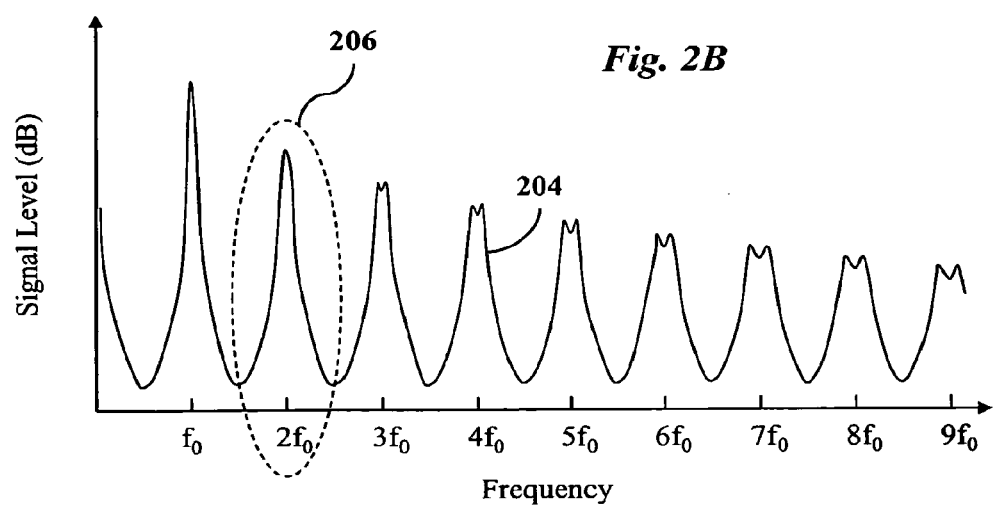
FIG. 2B is a graph of received signal level versus frequency for an MPI technique using intermodulation according to an embodiment of the invention.
Figure 2C:
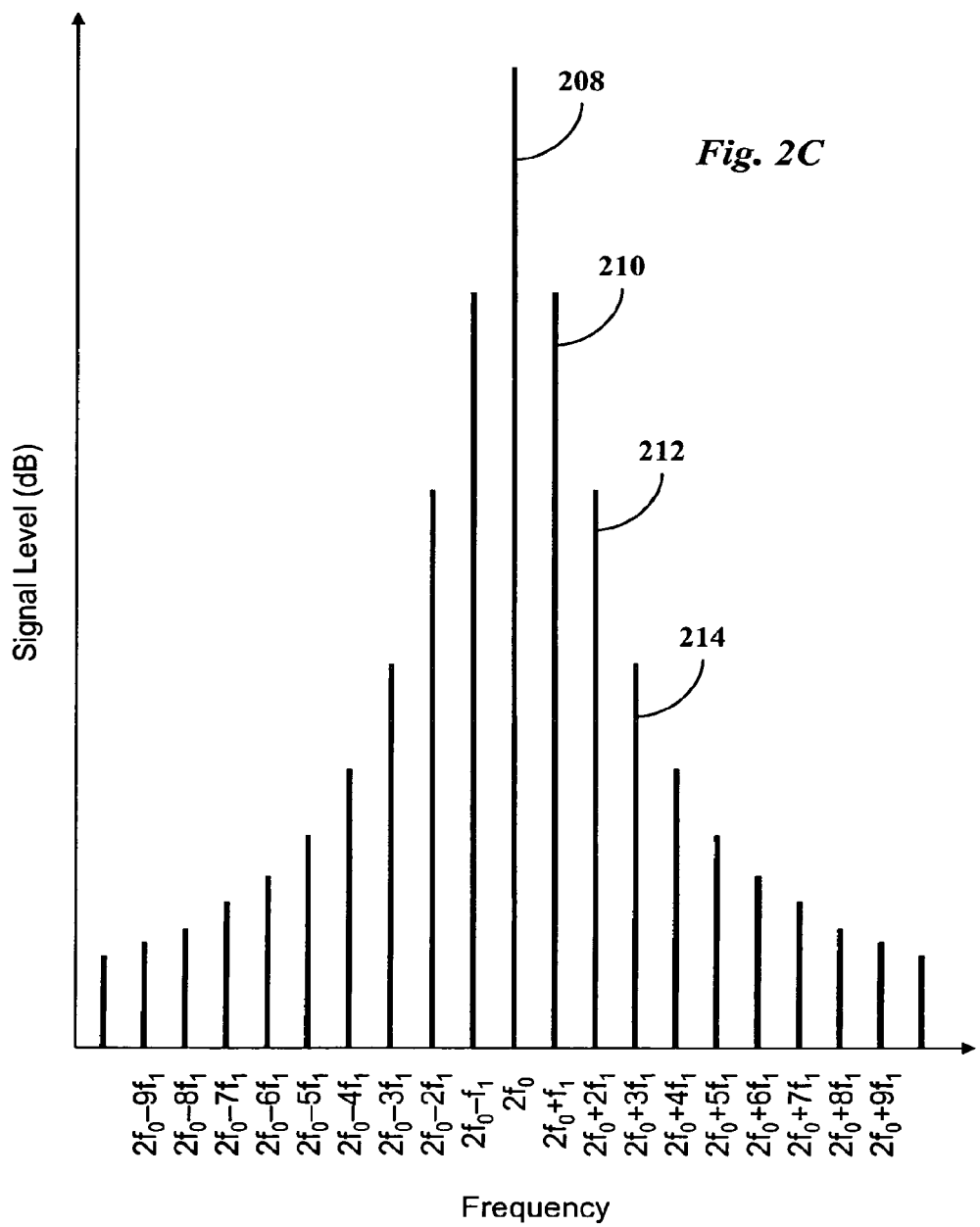
FIG. 2C is a graph of received signal level versus frequency detailing intermodulation tones contained in a single peak of the signal envelope shown in FIG. 2C.

FIG. 2B is a graph of received signal level versus frequency for an MPI technique using intermodulation according to an embodiment of the invention. The graph shows a simulated signal envelope 204 received by an untuned pickup coil. Intermodulation generates useful intermodulation products around the main harmonics, spreading the spectral information. These sideband intermodulation products around the main harmonics are absent in the conventional technique which does not use intermodulation. The amplitude and phase of the intermodulation products vary as a function of position. Each peak in the envelope actually contains multiple intermodulation sideband tones. For example, details of the tones contained in peak 206 around the second harmonic are shown in FIG. 2C. Tone 208 is the second harmonic ($2f_0$). Clustered around this harmonic are intermodulation tones such as tone 210 at frequency $2f_0+f_1$, tone 212 at frequency $2f_0+2f_1$, and tone 214 at frequency $2f_0+3f_1$. Because $f_0$ is significantly larger than $f_1$, the bandwidth required to receive the seven harmonics $2f_0$ through $8f_0$ in FIG. 2A is much larger than the bandwidth required to receive the seven intermodulation tones $2f_0-3f_1$ through $2f_0+3f_1$. As a result, intermodulation allows the use of a narrowband receiver to detect a similar number of distinct frequency signals. This, in turn, allows the use of a tuned receiver and improved signal to noise ratio (SNR).

Theory—Intermodulation

When magnetic field strengths used in MPI are less that 1 Tesla, tissue is unaffected by the magnetic field, but an SPIO particle undergoes a nonlinear change in magnetization described by the Langevin theory of paramagnetism. Specifically, the magnetization M is given by $$M = M_0 L\left[\frac{mH}{k_B T}\right] = M_0\left(\coth\frac{mH}{k_B T} - \frac{k_B T}{mH}\right)$$

where L is the Langevin function, m is the magnetic moment of the particle, H is the applied magnetic field, $k_B$ is Boltzmann's constant, and T is the absolute temperature.

To excite the particles, in some embodiments a single oscillating magnetic field of magnitude $H_0$ and frequency $f_0$ is generated within the region where the particles are located. In the case of a sinusoidal excitation waveform, the oscillating field is given by $$H(t) = H_0 \sin(2\pi f_0 t).$$

The field H(t) excites the particles and induces a corresponding time-varying magnetization at harmonics of $f_0$ $$M(t) = \sum_{m \geq 1} A_m \exp(2\pi i m f_0 t),$$

where $A_m$ are the amplitudes of the various harmonics and the index m ranges over the detected harmonics. See FIG. 2A.

In some embodiments using intermodulation, a second oscillating magnetic field of magnitude $H_1$ and frequency $f_1$ is also generated within the region where the particles are located. Thus, in the case of a sinusoidal excitation waveform aligned in parallel with the first excitation field, the net oscillating field is given by $$H(t) = H_0 \sin(2\pi f_0 t) + H_1 \sin(2\pi f_1 t).$$

This intermodulation field H(t) excites the particles the nonlinear Langevin function acts as a nonlinear mixer, inducing a corresponding time-varying magnetization $$M(t) = \sum_{m \geq 1} \sum_{n} A_{m,n} \exp(2\pi i (m f_0 + n f_1) t).$$

where $A_{m,n}$ are the amplitudes of the separate intermodulation tones. In addition to the harmonics, there are sideband tones corresponding to sum and difference frequencies. See FIGS. 2B-C. In practice, the index m is limited to a finite number of detected harmonics and the index n is limited by the finite number of detected sideband intermodulation tones around each harmonic. The rich intermodulation spectrum reveals the quantity of magnetic particles at the field-free point. Thus, instead of detecting a sequence of harmonics across a broad bandwidth, it is possible to obtain sufficient information by detecting the intermodulation signals across a relatively narrow bandwidth in close proximity to a single harmonic. Detecting intermodulation signals around additional harmonics provides additional information. For example, intermodulation sidebands may be detected around both second and third harmonics to produce a set of intermodulation images.

The frequencies $f_0$ and $f_1$ and the field strengths $H_0$ and $H_1$ can all be selected independently of each other. There are, however, trade-offs that guide their selection. Specific absorption rate (SAR) and received signal strength are dominated by $f_0$ and $H_0$ since $f_0 \gg f_1$ and SAR grows as $H^2 f^2$. Imaging speed and detection bandwidth are limited by $f_1$ to allow detection at each field-free point of intermodulation sidebands surrounding harmonics $m f_0$. Thus, the scanning speed is preferably restricted so that the sidebands can be detected at each point without aliasing. Although increasing $f_1$ can allow an increase in imaging speed, higher values for $f_1$ has other drawbacks because the received signal bandwidth must be less than the bandwidth of the receiver coil. SNR and the spatial extent of the point spread function (PSF) depend on the total magnitude of the excitation fields $H_{tot} = H_0 + H_1$. Increasing $H_{tot}$ increases the total signal received at the expense of widening the PSF. Increasing $H_1$ increases the received signal while affecting SAR negligibly. This allows trading increased signal for reduced resolution.

LF Intermodulation

In various embodiments, the LF (low frequency) intermodulation is preferably done by a frequency between 100 Hz and 5 kHz using water-cooled electromagnets. MRI gradient amplifiers may be used to drive the magnets, and the power requirements are reasonable. The LF intermodulation provides a large shift in magnetization of the particles with very little addition of SAR. It also allows large amounts of magnetic energy to be put into the sample which is then up-mixed with the RF frequency. An RF eddy current shield is used prevent interaction between the LF circuits and the RF transmit coil. In addition, a set of filters, such as common mode and differential low-pass filters, may also be positioned between the power amplifier and coil to reduce interaction. The gradient amplifiers are current controlled and eddy current compensated.

The LF excitation field may be implemented in x, y, z directions or any subset thereof. Changing the direction the LF excitation source changes the shape of the shape and magnitude of the point spread function.

The LF intermodulation fields and field-free point displacement fields may both be generated by the same electromagnets. However, because the power requirements for these fields differ, in other embodiments separate electromagnets are used to generate these two fields.

The transmit coils may be configured in various orientations and spatial arrangements. In one embodiment, the transmit coil is configured to create a transverse field along the length of the bore. Coils to create transverse excitation would require specialized and precise winding using known techniques.

The receive coil is a gradiometer constructed with litz wire and an overall $Q_{coil} = 167$. The coil has a diameter of 3.175 cm and the outer coil has a diameter of 4.5 cm. The receiver is a phase coherent control console and detector. The coherent detector directly samples at 65 MSPS and digitally down converts the RF signal to baseband.

The down-sampled signal has a bandwidth of 31.25 kSPS centered at $2f_0 = 300$ kHz with over 90 dB of dynamic range. An object containing a distribution of magnetic particles may be translated through the bore using a linear translator controlled by the control console. The detected signal is continuously acquired during translation of the stage in the readout direction, e.g., along the axis of the bore. The signal received by the pickup coil is fed to the preamplifier and then into the console. The digitized is quadrature demodulated at multiples of the intermodulation frequency (i.e., $\pm f_1$, $\pm 2f_1$, $\pm 3f_1$, $\pm 4f_1$, . . . ) and brick-wall filtered at 20 Hz. In practice, the intermodulation products around the fundamental are more difficult to receive than those around the harmonics due to eddy-current coupling from the excitation frequency into the receive coil. The intermodulation products around the fundamental may be detected by subtracting the fundamental using a low phase noise PLL or crystal filter. However, this would increase the complexity of the preamplifier.

The received signal contains most of the power in the lower harmonics and lower intermodulation peaks while most of the high frequency spatial content is in the higher harmonics and higher intermodulation peaks (where "higher" harmonics means m is greater than 4 and "lower" harmonics means m is 4 or less and, likewise, "higher" intermodulation peaks means n is greater than 4 and "lower" intermodulation peaks means n is 4 or less). The magnitude of the harmonics is strongly dependent on the size of the magnetic particles, and larger particles increase higher order harmonics. Intermodulation dramatically increases the spectral content of the received signal. The total normalized signal also is larger with intermodulation than without. The intermodulated point-spread function (PSF) is well-behaved around $2f_0$ and is similar to the PSF without intermodulation. As the absolute value of n or m increases, the magnitude of the PSF decreases and its resolution increases.

While in some embodiments the intermodulation products around a single harmonic (e.g., $2f_0 \pm n\, f_1$) may be received, in other embodiments the RF coils may be tuned to multiple frequencies to receive signals around multiple harmonics (e.g., $2f_0 \pm n\, f_1$, $3f_0 \pm n\, f_1$, $4f_0 \pm n\, f_1$, $5f_0 \pm n\, f_1$). For example, one or more dual-tuned coils may be used, each to receive signals around two harmonics. Alternatively, multiple RF coils may be separately tuned to receive the signals around each harmonic.

As $f_0$ increases, the frequency separation of its harmonics increases and simplifies coil-to-coil isolation, high-Q coil construction, and noiseless rejection of the fundamental. As $f_0$ increases, the SAR limit is rapidly approached. For example, with $f_0=1$ MHz and detection at $2f_0=2$ MHz, a SAR of 4 W/kg is reached at 3 mTpp is a small animal.

The high-Q receive coil dramatically simplifies construction and optimal noise matching of the signal detection system. The bandwidth requirements are low because of the low intermodulation frequency (e.g., $f_1=200$ Hz). With intermodulation, the receive bandwidth requirements are decreased compared to conventional MPI designs. More specifically, detecting N harmonics with conventional MPI would require bandwidth of BW=N $f_0$. Thus, detecting N=8 harmonics using an excitation frequency $f_0=150$ kHz would require a bandwidth of 1.2 MHz, resulting in sub-optimal matching to the preamplifier. With intermodulation, on the other hand, the bandwidth depends on $f_1=200$ Hz instead of $f_0=150$ kHz, and is thus very narrow in comparison.

Figure 5A:
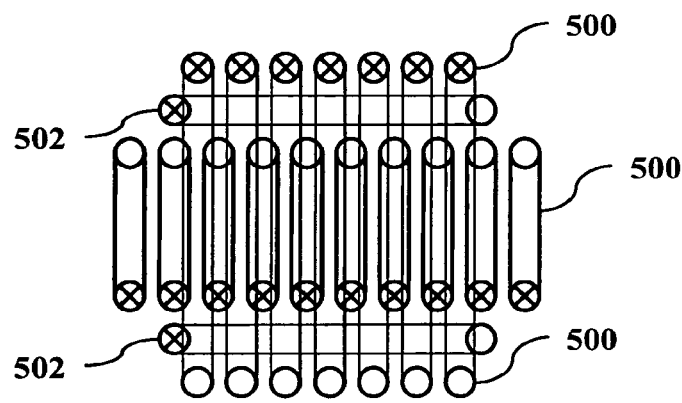
FIGS. 5A and 5B illustrate separate x, y, z coils used to measure signals in orthogonal x, y, z directions according to an embodiment of the invention.
Figure 5B:
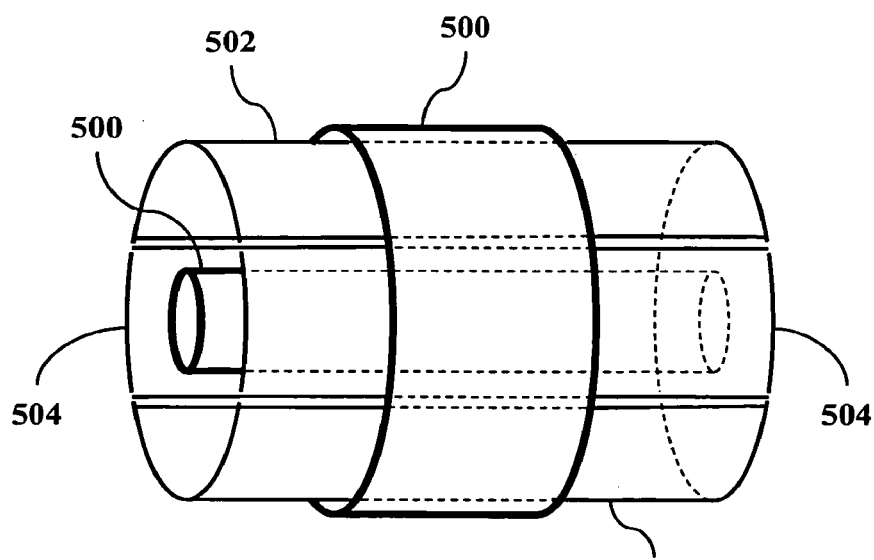

The specific system parameters above are provided for illustrative purposes and may be set to various other values or even varied dynamically during operation. The values of $H_0$ $H_1$ may be selected independently and each ranges from 0.01 to 100 mT, more practically ranges from 1 mT to 30 mT, and more preferably ranges from 10 mT to 20 mT. The gradient of the inhomogeneous field ranges from 0.5 T/m to 10 T/m, more practically ranges from 1 T/m to 7 T/m, and more preferably ranges from 2.5 T/m to 7 T/m. The value of $f_0$ ranges from 10 kHz to 10 MHz, more practically ranges from 20 kHz to 1 MHz, and more preferably ranges from 10 kHz to 1 MHz. The value of $f_1$ ranges from 1 Hz to 20 kHz, more practically ranges from 1 Hz to 5 kHz, and more preferably ranges from 1 Hz to 5 kHz. The value for $f_0$ is larger than that of $f_1$, more practically $f_0$ is 5 to 1,000,000 times $f_1$, and more preferably $f_0$ is 100 to 5,000 times Receiver Circuit The receiver pickup coils convert the magnetic signal from the sample into an electrical signal. In a preferred embodiment, separate x, y, z coils are used to measure signals in orthogonal x, y, z directions, as illustrated in FIGS. 5A and 5B. The cross-sectional view of FIG. 5A shows the z coil 500 and y coil 502. The perspective view of FIG. 5B also shows the z coil 500 and y coil 502 as well as the x coil 504. The z coil has zero net area and is wound as a gradiometer. The zero net area provides reduced feed through of the fundamental frequency $f_0$. If transverse RF transmit coils are used, the transverse receive coils can be geometrically decoupled by placing them such that less net area occurs between them. The receive coils are wound so that they would produce a homogeneous magnetic field. The transverse receive coils could also be wound with a gradiometer configuration.

Figure 4D:
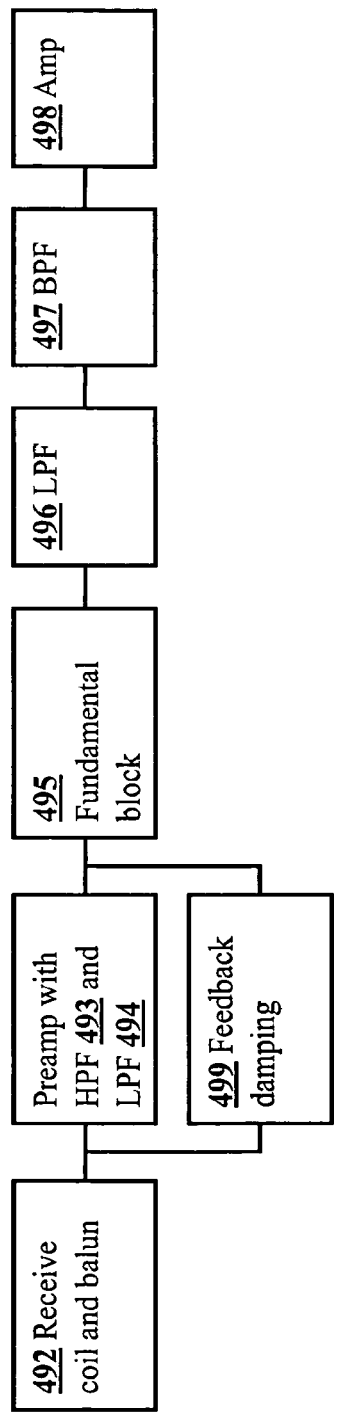
FIG. 4D is a block diagram of a receive circuit chain according to an embodiment of the invention.

FIG. 4D is a block diagram of a receive circuit chain according to another embodiment of the invention. Three such circuits may be used for x, y, z directions. Each circuit includes a high-Q receive coil and balus 492, low amplification and low noise HPF preamplifier 493 and 494, fundamental block 495, low-pass filter 496, band-pass filter 497, LPF amplifier 498, and feedback circuit 499. Band-pass filter 497 may be centered around a harmonic such as $2f_0$, but may also be centered around another higher harmonic or so that multiple harmonics are allowed to pass. The receive circuit is constructed to remove the fundamental signal $f_0$ and only pass harmonics $mf_0$, $m>1$. Those skilled in the art will appreciate that these circuits are illustrative examples and that various alternative circuits may be designed to perform equivalent functions.

The preamplifier uses operational amplifiers and high-Q tuned traps. The output may use an RC filter or bandpass filter to reduce high frequency noise.

Optimal matching between the receive coil and preamplifier occurs when the coil resistance at the receive frequency is equal to the ratio of the preamplifier noise voltage to the preamplifier noise current. The matching may be effected using baluns and matching capacitors and inductors in low-pass, high-pass, and band-pass configurations.

Figure 6A:
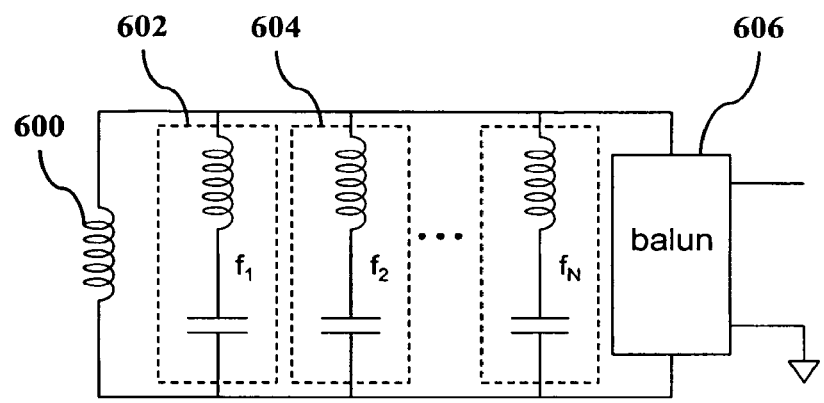
FIGS. 6A and 6B are circuit diagrams illustrating two alternative receive coil circuits for providing a multiply-tuned receive coil according to embodiments of the invention.
Figure 6B:
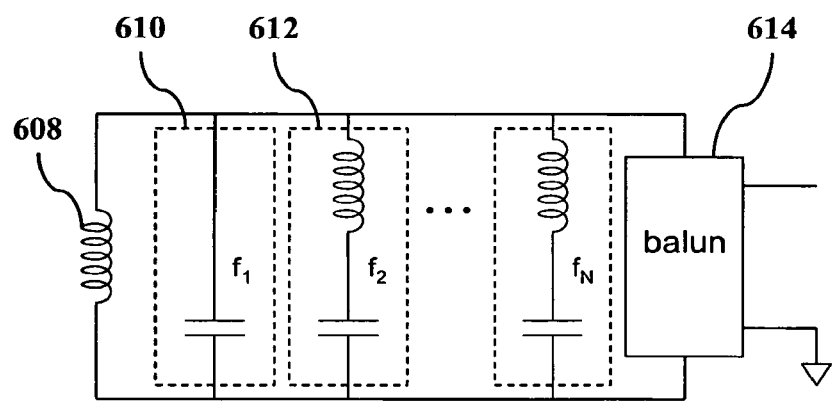

FIGS. 6A and 6B illustrate two alternative receive coil circuits for providing a dual-tuned or multi-tuned receive coil. The circuit of FIG. 6A includes receive coil 600, first frequency matching circuit elements 602, second frequency matching elements 604, and balun 606. Matching circuit elements 602 contain an inductor and capacitor tuned to a first frequency. Matching circuit elements 604 contain an inductor and capacitor tuned to a second frequency. The circuit of FIG. 6B includes receive coil 608, first frequency matching circuit elements 610, second frequency matching elements 612, and balun 614. Matching circuit elements 610 contain a capacitor tuned to a first frequency. Matching circuit elements 612 contain an inductor and capacitor tuned to a second frequency. As shown in the figures, additional frequency matching elements may be added to the circuits of FIG. 6A or 6B in a similar manner to provide matching to N distinct frequencies for a multi-tuned coil.

Theory—SNR and Noise Matching

When the receive coil and preamplifier dominate the noise in a receiver, it is important to noise match the receiver to the pickup coil to improve SNR. Optimal matching occurs when the coil impedance is matched to the voltage and current noise of the preamplifier. Because the coil contains reactive impedance, it is not possible to achieve a high-bandwidth match. Assuming optimal matching, the dominant noise source is the coil. A high-Q receiver coil and bandwidth narrowing will increase preamplifier SNR for a given $f_0$ by reducing the preamplifier noise figure, the coil noise for a given volume, and the detection bandwidth. Additionally, because these factors are independent of $f_0$, the detection frequency can be increased to reach body noise dominance without increasing receiver bandwidth. Moreover, the imaging region can be increased by increasing $H_{tot}=H_0+H_1$. Embodiments of the present invention thus provide narrowband MPI which increases SNR for a fixed SAR.

The signal from the MPI receive coil is amplified prior to digitization. The amplifier noise is minimized when the receiver coil is noise matched to the preamplifier. Specifically, noise matching is optimized by minimizing the ratio of output noise to input noise, i.e., the noise gain ratio. This ratio is minimized when the real coil resistance at resonance is $R_{coil}=e_n/i_n$, where $e_n$ and $i_n$ are, respectively, the voltage and current noise amplitude per unit bandwidth of the preamplifier.

Operation

In medical imaging applications, magnetic nanoparticles may be components of a contrast agent that may be distributed in any object, e.g., by injection into an organism or labeled into or onto cells. The object, which may be animate or inanimate, human, animal, or other organism or portion thereof, is then positioned into the apparatus for imaging. To detect the concentration of magnetic particles in different regions, the field-free point is moved relative to the object by physical motion of the organism relative to the apparatus and/or displacement of the field-free point by dynamically changing the magnetic field. For example, movement of the field-free point can be produced by a combination of physical translation in the axial direction with dynamic scanning in the transverse plane. The scanning can also be produced by physical translation alone or dynamic scanning alone.

At each field-free point, one or more oscillating magnetic fields may be used to excite the magnetic particles situated at the field-free point. These oscillating fields typically have amplitudes in the range of 0.1 mT to 20 mT. These fields cause the magnetization of the particles to saturate, generating harmonics that can be isolated from the fundamental using frequency domain techniques. The harmonic response at each field-free point is detected using one or more receive coils, and the detected signals are recorded at each point to create a complete scan of the distribution of particles in the imaging region.

Imaging

The complex interplay between a magnetic particle and the field-free point corresponds to a point-spread function that depends on various factors such as the particle size, magnetic field gradient, and intermodulation product. The measured PSF has higher SNR in sidebands closer to the harmonic (e.g., $2f_0$ and $2f_0 \pm f_1$), but contains more high frequency spectral content in the sidebands further from the harmonic (e.g., $2f_0 \pm 2f_1$, $2f_0 \pm 3f_1$, $2f_0 \pm 4f_1$, ...).

In some embodiments, the high SNR of the lower sidebands may be combined with the higher resolution of the upper sidebands to form a reconstructed image. In the reconstructed image, if the upper sidebands become unavailable as SNR drops, then the image resolution decreases.

Dynamic Gradient Reduction

Dynamic gradient reduction—Dynamically reducing the gradient during imaging enables increase of the imaging area. This increases SNR at the expense of the point spread function (resolution). We can then dynamically change this over time so we can choose the desired resolution/SNR tradeoff. This is implemented using a second strong gradient in the opposite direction using electromagnets, but it could also be done by physically moving the permanent magnets.

Excitation Waveforms

The RF excitation signal is a periodic oscillating field, such as a sinusoidal waveform. However, the waveform of the RF excitation is not necessarily sinusoidal. Similarly, the LF intermodulation excitation signal is a periodic oscillating field, and it may be a sinusoidal waveform or non-sinusoidal waveform. In fact, non-sinusoidal waveforms are preferable in some embodiments, as they can provide more harmonic content, improving SNR and resolution. For example, embodiments of the invention may use a triangle waveform. The waveform may also be dynamically changed during operation to provide different imaging properties.

In some embodiments, intermodulation may be applied separately and sequentially to the excitation field in the x, y, and z directions. For example, intermodulation may be applied in the x direction alone, while no intermodulation is used in either the y or z directions. Then intermodulation may be applied to just the y direction, and then just to the z direction. The intermodulation may also be applied in a combination of directions at once, e.g., a rotating x-y field created by phase-shifted x and y intermodulation waveforms.

Receiver Signal Processing

We use a dual-lock in amplifier system to receive the signal. The signal is downmixed centered at two and three times the high-frequency RF excitation. The downmixed signal is then downmixed again at the $LF^*(0, +/-1, +/-2, +/-3, \ldots)$.

The signal from the receive coil and preamplifier chain is fed into a digital down-converter circuit block that down-converts the signal to baseband with channelization. The circuit block independently down-samples each intermodulation signal so that each subband tone is channelized. For example, intermodulation products 210, 212, 214 shown in FIG. 2C are separately down-converted and sampled. During operation, these intermodulation products are continuously sampled and stored, associating the stored signal with a corresponding position of the field-free region.

Figure 7A:
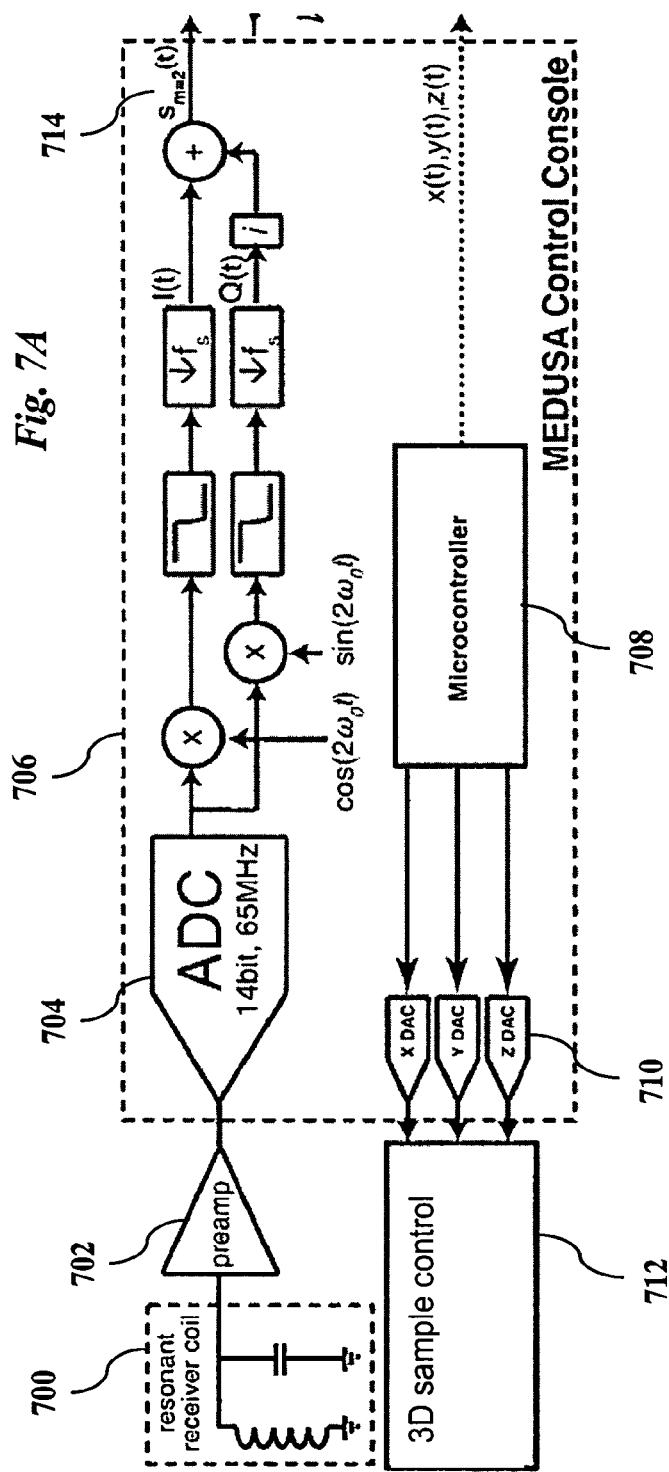
FIGS. 7A and 7B are block diagrams of signal processing circuit blocks used to process the signals from the receive coil circuit chains, according to an embodiment of the invention.
Figure 7B:
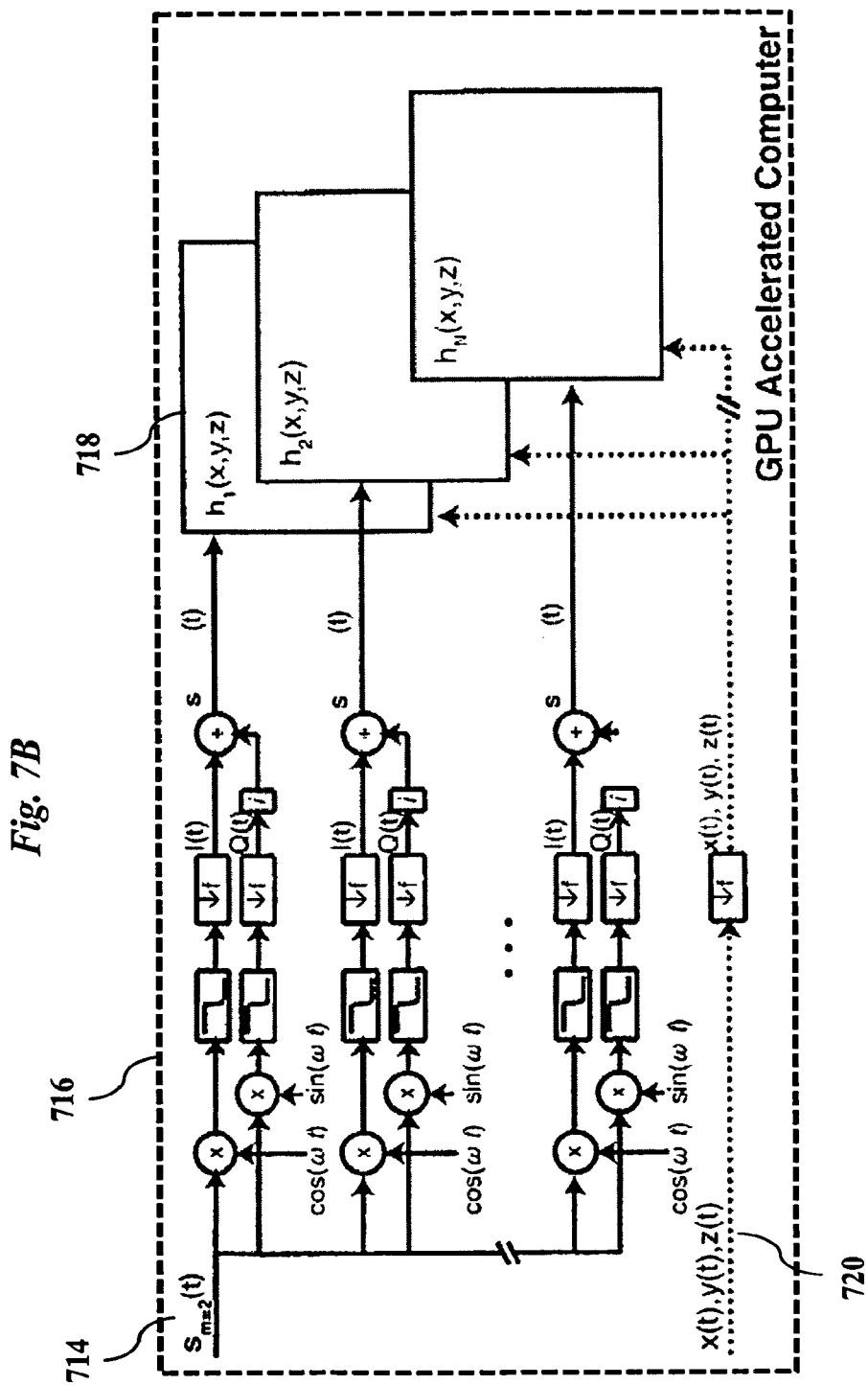

FIGS. 7A and 7B are block diagrams of signal processing circuit blocks used to process the signals from the receive coil circuit chains. The circuit block 706 of FIG. 7A receives signals originating from the receiver coil 700 and preamplifier 702. The signals are digitized by 14 bit 65 MHz analog-to-digital converter 704 and then separated into in-phase and quadrature signal components and down-sampled to produce corresponding components I(t) and Q(t) of digital signal 714, $s_{m=2}(t)$. This signal preferably has a bandwidth of 32 kHz to 100 or more kHz. Block 706 also contains microcontroller 708 which provides x(t), y(t), z(t) control signals to 3D sample control block 712 in order to control relative 3D translation between the sample and the field-free point. Digitized signal 714 is fed into processing block 716 of FIG. 7B where its intermodulation products are independently channelized and down-sampled to produce in-phase and quadrature component signals I(t) and Q(t) for each of N subbands around the harmonic. These N subband signals are then stored according to associated x(t), y(t), z(t) position coordinates 720 in N corresponding image memory blocks $h_1(x,y,z), \ldots, h_N(x,y,z)$, such as block 718. The processing blocks of FIG. 7B may be implemented by a GPU accelerated computer or using an FPGA or ASIC.

Field-Free Point Translation Magnets

Field-free point translation electromagnets may be used to translate the position of the field-free-point in real time to provide scanning. In one embodiment, a pair of coils is used to provide independent translation in each of three orthogonal directions. Due to the strong field gradient, the electromagnets are required to generate strong fields to provide significant displacement. For example, 5 kW magnets provide a 4.5 cm translation. The magnets preferably have a 1% homogeneity. To provide cooling, the coils may be made of hollow copper tubing through which water may be circulated at 6 gpm and 30 psi providing 34 kW cooling capacity. The RF shield absorbs significant power and may also be actively cooled using circulating water.

Scanning

Figure 8:
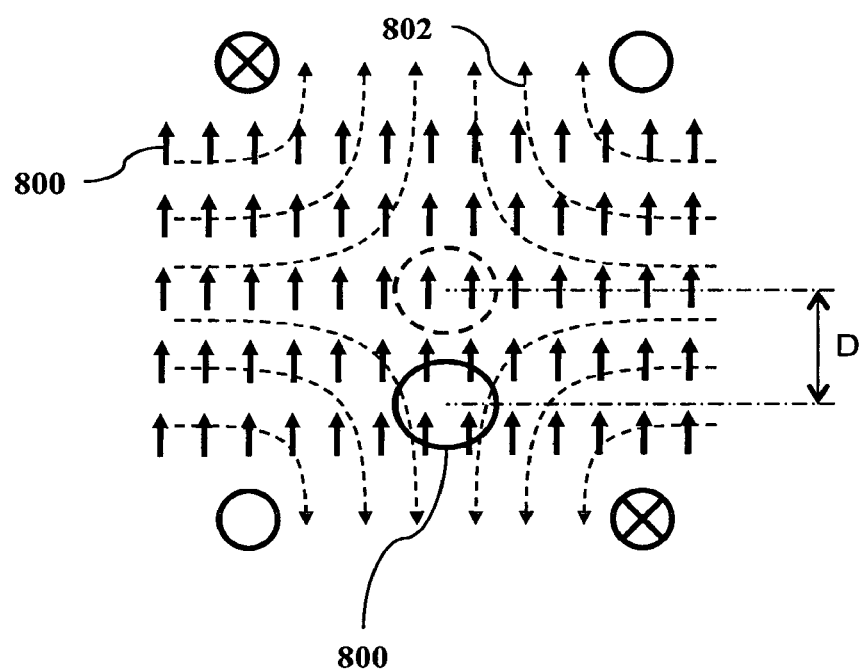
FIG. 8 illustrates the use of a homogeneous field superimposed on an inhomogeneous gradient field to shift the position of the field-free point, according to an embodiment of the invention.

Movement of the field-free point relative to the sample may, in general, be performed in one, two, or three dimensions, and may be implemented by mechanical movement of the sample relative to the magnets and/or by electronically modifying the inhomogeneous gradient field using electromagnets that generate a homogeneous field. These field displacement electromagnets can be implemented in x, y, and z directions, or a subset of these directions. In a combination system, for example, electromagnets provide scanning of the field-free point within a plane while mechanical movement provides translation along an axial direction perpendicular to the plane. The electronic displacement of the field-free point is preferably performed using a homogeneous field created by electromagnets, e.g. using Helmholtz coils. The homogeneous field 800 superimposed on the inhomogeneous gradient field 802 has the effect of shifting the position of the field-free point 804 by a distance D, as illustrated in FIG. 8. A switching amplifier such as an H-bridge may be used to reverse the direction of the homogeneous field to provide displacement of the field-free point in opposite directions along a given axis. In some embodiments, the LF excitation magnets are the same as the magnets used to translate the field-free point. These dual-purpose electromagnets are driven by the LF excitation signal as well as the slower scanning displacement signal.

Due to the large field gradients, strong homogeneous fields are required to shift the field-free point a significant distance to provide electronic scanning of the sample. Consequently, scanning a large field of view can require enormous amounts of power and large amplifiers. Accordingly, embodiments of the present invention provide methods to scan that reduce heat loading of the power amplifiers, allowing the use of smaller and less expensive power electronics. For example, FIG. 9 illustrates an example of a power-efficient scanning trajectory in the x-y plane according to one embodiment of the invention. The scan begins with a left-to-right scan line 900 along the x-axis. Line 900 is displaced at a large distance in the y-direction from center line 916. Center line 916 is the line along which the field-free point is positioned when there is no displacement field in the y-direction. Thus, scan line 900 requires a strong field. Horizontal scan line 900 is followed by a diagonal scan line down and to the left to the start of horizontal scan line 902 which is displaced a small distance in the y-direction from center line 916, and thus requires only a weak field. Horizontal scan line 902 is followed by a diagonal scan up and to the left to the start of horizontal scan line 904, which is displaced slightly less from center line 916 than scan line 900. Next is scan line 906, which is displaced slightly more from the center line 916 than scan line 902. The scan then continues in this way, alternating between scan lines above and below center line 916. The consecutive scan lines above and below the center line 916 are separated by approximately the same distance due to the progressive decrease in displacement of y-displacement of scan lines above the center line 916 and progressive increase of y-displacement of scan lines below the center line 916. Consequently, as power demands for scan lines displaced in one direction decrease, power demands in scan lines displaced in the other direction increase, resulting in an approximately constant average power demand. This constant average power correlates to the uniform distance between consecutive scan line pairs, i.e., the displacement between lines 900 and 902 is the same as the displacement between lines 904 and 906, between lines 908 and 910, and between lines 912 and 914. Switching between displacements above and below the center line 916 also has the benefit that it allows circuits used for displacements in one direction to cool during a scan displaced in the opposite direction. Depending on the application and operational parameters of a given scan, each line may take anywhere from 1 ms to 0.5 s. Because the horizontal scan lines all scan in the same direction, i.e., from left to right, the signal processing is simpler.

Other scanning trajectories are also possible, of course, and may be used depending on the specific application or scanning requirements. For example, to reduce transition time from scan line to scan line in the above example, instead of going to the next scan line diagonally, it is possible to change only the y-displacement when going to the next scan. The amplifiers have slew rate limits, and this would reduce the slew rate requirements in the x-direction. For example, if heating is not a significant issue then a more time-efficient scan may be used, such as a serpentine scan of horizontal lines sequentially progressing from a largest upward displacement in the y-direction to a largest downward displacement in the y-direction. Alternatively, a time-efficient spiral scan may be performed, starting from the center and spiraling outward. The spiral scan has the advantage that more of the scanned region is likely to overlap with the sample than a rectangular scan.

Adaptive Scanning

Embodiments of the invention provide techniques for adaptive scanning to improve efficiency. According to one method of adaptive scanning, an initial scout scan is performed at lower resolution. The low resolution scan may be performed quickly by optimizing signal acquisition to just the first and/or second and/or third harmonics, which would require less time to acquire than a high resolution scan. The low resolution scan can sample points in the imaging region at a lower spatial density. For example, FIGS. 10A and 10B illustrate a technique of adaptive multi-resolution scanning. The imaging region 1000 shown in FIG. 10A is scanned quickly at a low resolution, sampling at each of the sample points such as point 1002. A subset of the sample points have a detected signal, such as sample point 1004. The resulting image is then analyzed to identify within the imaging region 1000 an approximate perimeter 1006 containing sample points such as point 1004 where the magnetic particles were detected. Using this information, a higher resolution scan can be performed within the identified perimeter, as shown in FIG. 10B. The spatial density of sample points, such as point 1008, is much higher than in the low resolution scan. This technique can reduce total scan time because the low resolution scan can be performed relatively quickly and is then used to eliminate time that would otherwise be wasted during a slower high resolution scan of the entire imaging region.

The high-resolution scan can involve using a dynamic gradient reduction technique which involves dynamically changing the gradient strength. It can also include modifying the waveform and amplitude of the intermodulation field, and careful choice of the acquisition trajectory. Most of the reduction in acquisition time will be through choosing a mathematically optimal acquisition trajectory that will change on the fly, i.e., as more data is acquired, the system determines where to look for more signal and where to refine.

As an alternative to the two-step adaptive scanning technique described above, the acquisition of low and high resolution signals may be performed on a point-by-point basis during one scan. Specifically, the imaging region may be scanned as follows. At each coarse low-resolution sample point a signal is acquired, as described above in relation to FIG. 10A. Importantly the coarse sampling is finer or comparable to the resolution of the first scan; the fine sampling is finer or comparable to the resolution of the highest harmonic or intermodulation image. However, before proceeding to scan the next coarse data point, the low-resolution signals at the current coarse data point are examined to determine if there is a significant detected signal indicating the presence of magnetic particles in the entire "super pixel" surrounding this coarse sample point. If so, then a high-resolution sampling of the "super-pixel" surrounding the coarse point is then performed and the signals are acquired at a high resolution sampling structure. The scan then proceeds to the next coarse sample point and repeats the process until the entire imaging region is scanned. Of course, more complex schemes than this could also be employed. For example, if the N signals at the center of the super-pixel could be used to vary the instantaneous sampling distance from only one sample per super-pixel to fully sampled at the finest resolution of the highest harmonic or intermodulation image.

Image Reconstruction

Figure 11:
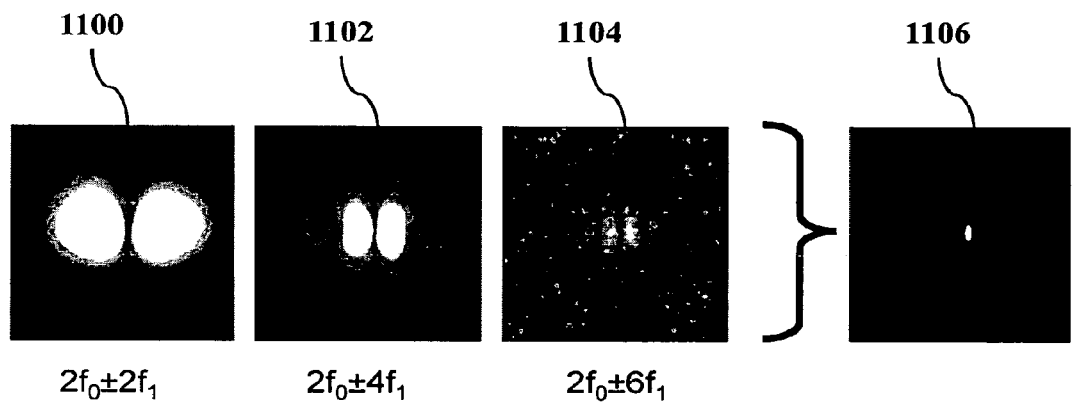
FIG. 11 shows how multiple harmonic images are all different measurements of the same point source.

In embodiments of the invention, detected signals from different harmonics and/or intermodulation sidebands are separately down-converted and stored to form a set of N distinct images $h_1(x,y,z), \ldots, h_N(x,y,z)$, each corresponding to a different frequency. Each of these images is a convolution of the unknown magnetization. An image may be reconstructed by a method of parallel deconvolution of these images to form a single composite image. According to one such method, a Fourier transform is applied to each of the detected signals $s_n(x,y,z)$ to obtain a frequency-domain representation, $Y_n(k)=F[s_n(x,y,z)]$, where k is a vector indexing the frequency domain and F is the Fourier transform. Now let $H_n(k)$ represent the n-th harmonic point spread function of a point source (which can be determined by calibration using a magnetic particle smaller than the system's resolvable limit), and let M(k) be the unknown magnetization distribution in the frequency domain (i.e., the Fourier transform of the unknown magnetization distribution in the spatial domain). Then we have $Y_n(k)=H_n(k)M(k)+N_n(k)$, where $N_n(k)$ is the Fourier transform of the unknown n-th harmonic noise image. Hence, finding the desired M(k) is equivalent to finding the slope of a complex line given the regression data $\{Y_n(k),H_n(k)\}$. There are many ways of finding the slope, e.g., using a least-squares fit. The reconstructed composite image in the frequency domain is then given by $M(k)=H^{T*}(k) \cdot Y(k)/(H^{T*}(k) \ H(k))$, where H(k) and Y(k) are N-dimensional column vectors whose components are $H_n(k)$ and $Y_n(k)$, respectively. The reconstructed composite image is then $m(x,y,z)=F[M(k)]$. This method solves for each frequency-domain point separately. Because the least-squares problem grows linearly with the number of points, it is not the computationally limiting factor, as the fast Fourier transform (FFT) used to prepare the data scales with O(N·log N). FIG. 11 illustrates the parallel deconvolution of multiple frequency images 1100, 1102, 1104 to produce a composite image 1106.

The reconstruction method just described above will amplify noise at higher-frequency points in the frequency domain where SNR in the reference images are low. Accordingly, embodiments of the invention provide the following technique to address this issue. A simple non-linear processing step may be used to gracefully degrade reconstructed image resolution while improving the composite image. Specifically, points in the frequency domain with insufficient SNR may be set to zero:

$$M(k) = \begin{cases} 0 & \sum_{n=1}^{N} |H_n(k)| < \varepsilon \\ H^{T*}(k) \cdot Y(k)/(H^{T*}(k) \cdot H(k)) & \text{otherwise} \end{cases}$$

where ε is an experimentally determined threshold that depends on the SNR. In an alternative thresholding technique, each element where $|H_n(k)|>\varepsilon$ is used and the others are removed. That is, $$G_n(k) = \begin{cases} 0 & |H_n(k)| < \varepsilon \\ H_n(k) & \text{otherwise} \end{cases}$$

$$M(k) = \begin{cases} 0 & \sum_{n=1}^{N} |G_n(k)| = 0 \\ G^{T*}(k) \cdot Y(k)/(G^{T*}(k) \cdot G(k)) & \text{otherwise} \end{cases}$$

The parallel deconvolution technique described here can theoretically increase the SNR of the composite image by $\sqrt{N}$, but will provide somewhat less gain at high spatial frequencies, where fewer harmonics are used in the image reconstruction. For regions of k-space where none of the N harmonics or intermodulation terms satisfy the condition $|H_n(k)|>\varepsilon$, then this region of k-space M(k) is set to zero. Then m(x,y,z) is computed by an inverse FFT algorithm in a computer.

Gradient Magnet Configurations

Figure 12A:
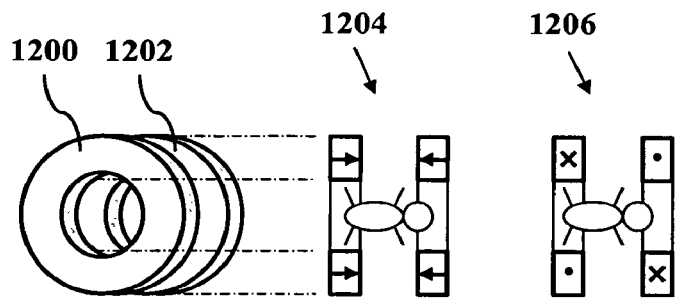
FIGS. 12A, 12B, 12C illustrate three designs of gradient magnet configurations which may be used in different embodiments of the invention.
Figure 12B:
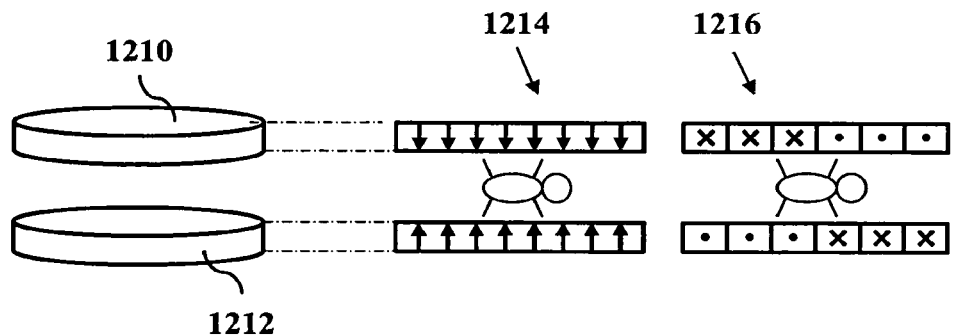
Figure 12C:
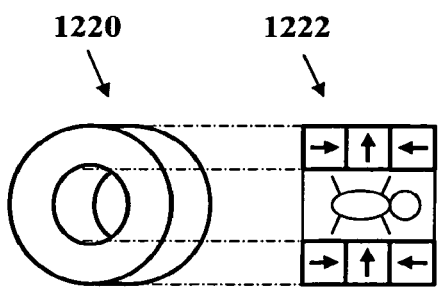

Various designs and configurations of gradient magnets may be used in various embodiments of the invention. The gradient magnets may be permanent magnets, electromagnets, or a combination of both. The gradient magnets may also be superconducting magnets. Three examples of gradient magnets are illustrated in FIGS. 12A, 12B, 12C. A front entry design using ring magnets 1200, 1202 is shown in FIG. 12A. Also shown are cut-away views in the case where the rings are permanent magnets 1204 and electromagnets 1206. A side entry design using circular plate magnets 1210, 1212 is shown in FIG. 12B. Also shown are cut-away views in the case where the discs are permanent magnets 1214 and electromagnets 1216. FIG. 12C shows, in perspective view 1220 and cut-away view 1222, a front entry design using a ring magnet array configuration which improves field strength for a given bore diameter.

FIG. 13A is a cross-sectional illustration of a pair of a specially designed arrangement of magnets 1300 and 1302 that produce a strong field gradient and a field-free line 1304. The permanent magnet arrangement is a three dimensional structure that can be machined from a block of permanent magnets, and is designed using an $L^1$-norm optimization method. In one embodiment, the magnet is designed so that there is an axial entry and the field free line is perpendicular to the axis of the magnet. The magnet or the sample being imaged can be rotated mechanically.

The field-free line (which need not be perfectly straight) allows magnetic particles in an entire one-dimensional region to be detected at once. Electromagnets or physical translation may be used to shift the field-free line relative to the sample, based on the same principle as shifting the field-free point in other embodiments. Moreover, rotation of the field-free line relative to the sample, e.g., by geometric rotation of the permanent magnets and field shifting magnets relative to the sample, allows computed tomography techniques to be used for image reconstruction. For example, FIGS. 13B and 13C show a sample 1304 being imaged using such a technique. In FIG. 13B the field free line 1308 is displaced in a direction perpendicular to the line to various other positions such as 1306. At each position of the line, data is acquired. The data from all the line positions is then used to form an image slice. The orientation of the field-free line relative to the sample 1304 is then changed, as shown in FIG. 13C, by rotating the gradient magnets together with the field shifting magnets relative to the sample. The field-free line is then displaced again to various positions such as 1310 and 1312, and data is again acquired at each position of the field-free line to form an image slice. Thus, a collection of image slices are acquired, each having a unique angle associated with it. For example, image slices may be acquired for a collection of distinct angles ranging uniformly over 180 degrees. Computed tomographic techniques are then used to generate an image of the sample from the collection of image slices. The field-free line allows for a projection format for MPI, dramatically decreasing the time required to image an object.

The invention claimed is:

1. A method of magnetic particle imaging, comprising:
placing magnetic particles into an imaging region;
generating within the imaging region an inhomogeneous magnetic field having a spatial gradient and having a field-free region within the imaging region;
generating within the imaging region a scanning magnetic field that displaces the position of the field-free region, wherein the scanning magnetic field causes the position of the field-free region to follow a predetermined trajectory;
generating an excitation magnetic field that excites the magnetic particles positioned at the field-free region;
detecting signals produced by the magnetic particles distributed within the imaging region, wherein the signals detected at a given time are produced by magnetic particles located at positions coincident with a position of the field-free region at the given time; and
producing from the detected signals an image of the distribution of the magnetic particles within the imaging region,
wherein a frequency of the scanning magnetic field is lower than a frequency of the excitation magnetic field, and
wherein the scanning magnetic field is a homogeneous magnetic field.

2. The method of claim 1 wherein placing the magnetic particles in the imaging region comprises placing an object, such as an organism or portion thereof, in the imaging region, wherein the object contains a distribution of the magnetic particles.

3. The method of claim 1 wherein the predetermined trajectory includes a sequence of scan lines, and wherein an average displacement between pairs of sequential scan lines is approximately constant.

4. The method of claim 1 wherein the trajectory includes a set of parallel scan lines, and wherein the trajectory moves in the same direction for all the parallel scan lines.

5. The method of claim 1 wherein the trajectory has a spiral pattern.

6. The method of claim 1 wherein the trajectory has a serpentine pattern.

7. The method of claim 1 wherein the scanning magnetic field causes the position of the field-free region to move along a first axis at a first average rate and to move along a second axis at a second average rate, wherein the first axis is perpendicular to the second axis, and wherein a ratio of the first average rate to the second average is between 64 and 1024.

8. The method of claim 1, wherein said generating said excitation magnetic field is performed without using any magnets used for said generating said scanning magnetic field.

9. The method of claim 1, wherein said generating said excitation magnetic field is performed without using any magnets used for generating said inhomogeneous magnetic field having the spatial gradient and the field-free region.

10. The method of claim 1 wherein said generating said excitation magnetic field is performed without using any magnets used for said generating said inhomogeneous magnetic field having the spatial gradient and the field-free region,
wherein said generating said excitation magnetic field is performed without using any magnets used for said generating said scanning magnetic field.

11. The method of claim 1, wherein the scanning magnetic field causes the position of the field-free region to linearly translate.

12. The method of claim 11, wherein the scanning magnetic field further causes the position of the field-free region to linearly translate for a period of 1 ms-0.5 s.

13. The method of claim 1, further comprising displacing the position of the field-free region with respect to a sample comprising the magnetic particles using mechanical movement.

14. The method of claim 1 wherein the predetermined trajectory contains a sequence of scan lines.

15. A method of magnetic particle imaging, comprising:
placing magnetic particles into an imaging region;
generating within the imaging region an inhomogeneous magnetic field having a spatial gradient and having a field-free region within the imaging region;
generating within the imaging region a scanning magnetic field that displaces the position of the field-free region, wherein the scanning magnetic field causes the position of the field-free region to follow a predetermined trajectory;
generating an excitation magnetic field that excites the magnetic particles positioned at the field-free region;
detecting signals produced by the magnetic particles distributed within the imaging region, wherein the signals detected at a given time are produced by magnetic particles located at positions coincident with a position of the field-free region at the given time; and
producing from the detected signals an image of the distribution of the magnetic particles within the imaging region,
wherein the predetermined trajectory alternates between scan lines positioned on opposite sides of a central position of the field-free region.

16. A magnetic particle imaging device, comprising:
a magnetic field generating apparatus arranged proximate an imaging region of the magnetic particle imaging device, the magnetic field generating apparatus being configured to produce a magnetic field within the imaging region of the magnetic particle imaging device such that the magnetic field will have a field-free region (FFR) for an object under observation that contains a magnetic tracer, the magnetic field generating apparatus being further configured to produce a translating magnetic field that translates the position of the FFR, the magnetic field generating apparatus being further configured to produce an excitation magnetic field that induces a signal from the magnetic tracer in the object under observation, wherein the excitation magnetic field is produced by a different magnet system than a magnetic system that produces the translating magnetic field and the magnetic field having said FFR;

a receiver arranged proximate the observation region, the receiver being configured to receive the signal from the magnetic tracer in the observation region; and a signal processor configured to be in communication with the receiver, the signal processor being configured to convert the signal into an image of the magnetic tracer, wherein a frequency of the translating magnetic field is lower than a frequency of the excitation magnetic field, and wherein the translating magnetic field is a homogeneous magnetic field.

17. The device of claim 16, wherein the magnetic field generating apparatus is configured to produce the magnetic field that has the FFR and to produce the translating magnetic field that translates the position of the FFR with separate magnetic systems.

18. The device of claim 16, wherein the magnetic field generating apparatus is further configured to produce said translating magnetic field such that said translating magnetic field causes the position of the field-free region to translate a distance of at least 1 cm through a course of obtaining the signal.

19. The device of claim 16, wherein the magnetic field generating apparatus is further configured to produce said translating magnetic field such that said translating magnetic field causes the position of the field-free region to linearly translate.

20. The device of claim 19, wherein the magnetic field generating apparatus is further configured to produce said translating magnetic field such that said translating magnetic field causes the position of the field-free region to linearly translate for a period of 1 ms-0.5 s.

21. The device of claim 16, wherein the magnetic field generating apparatus is configured to produce the magnetic field within the imaging region of the magnetic particle imaging device such that the magnetic field has a gradient of 0.5 to 10 T/m.

22. The device of claim 16, wherein the magnetic field generating apparatus is configured to produce the magnetic field within the imaging region of the magnetic particle imaging device such that the magnetic field has a gradient of 2.5 to 7 T/m.

23. The device of claim 16, further comprising a linear translator configured to displace the position of the field-free region with respect to a sample comprising the magnetic particles using mechanical movement.

* * * * *